(12) United States Patent
Benaron et al.

(10) Patent No.: US 6,748,259 B1
(45) Date of Patent: Jun. 8, 2004

(54) OPTICAL IMAGING OF INDUCED SIGNALS IN VIVO UNDER AMBIENT LIGHT CONDITIONS

(75) Inventors: David A. Benaron, Portola Valley, CA (US); Yair Talmi, Newtown, PA (US); Ilian H. Parachikov, Fremont, CA (US)

(73) Assignee: Spectros Corporation, Portola Valley, CA (US)

( * ) Notice: Subject to any disclaimer, the term of this patent is extended or adjusted under 35 U.S.C. 154(b) by 285 days.

(21) Appl. No.: 09/595,370

(22) Filed: Jun. 15, 2000

(51) Int. Cl.$^7$ .................................................. A61B 6/00
(52) U.S. Cl. ....................... 600/476; 600/477; 600/478; 356/456; 356/364; 356/433; 250/334.22; 250/341.3
(58) Field of Search .................. 600/476, 478, 600/477, 473, 475; 128/898, 894; 382/128, 130; 356/456, 364, 433; 250/339.02, 461.2

(56) References Cited

U.S. PATENT DOCUMENTS

| | | | |
|---|---|---|---|
| 4,608,990 A | | 9/1986 | Elings |
| 5,213,105 A | | 5/1993 | Gratton et al. ............... 128/664 |
| 5,371,368 A | * | 12/1994 | Alfano et al. ............. 250/341.1 |
| 5,386,827 A | * | 2/1995 | Chance et al. ............... 600/310 |
| 5,601,087 A | | 2/1997 | Gunderson et al. ......... 128/664 |
| 5,647,368 A | | 7/1997 | Zeng et al. .................. 128/665 |
| 5,648,269 A | | 7/1997 | Lakowicz et al. ............. 436/68 |
| 5,672,333 A | | 9/1997 | Rajagopalan et al. ........ 424/9.6 |
| 5,699,798 A | | 12/1997 | Hochman et al. |
| 5,865,754 A | | 2/1999 | Sevick-Muraca et al. ... 600/476 |
| 5,919,140 A | | 7/1999 | Perelman et al. ........... 600/476 |
| 5,928,627 A | | 7/1999 | Kiefer et al. ................. 424/9.6 |
| 5,936,731 A | | 8/1999 | Cabib et al. ................. 356/346 |
| 6,091,983 A | * | 7/2000 | Alfano et al. ............... 600/431 |

FOREIGN PATENT DOCUMENTS

| | | |
|---|---|---|
| WO | WO 93/13395 | 7/1993 |
| WO | WO 96/32892 | 10/1996 |
| WO | WO97/36619 | 10/1997 |
| WO | WO98/10698 | 3/1998 |
| WO | WO98/48846 | 11/1998 |
| WO | WO 99/53832 | 10/1999 |

OTHER PUBLICATIONS

Lam, Stephen, et al., "Detection of Early Lung Cancer Using Low Dose Photofrin II", *CHEST*, vol. 97, No. 2, Feb. 1990, pp. 333–337.

Ballou Byron, et al. "Tumor labeling in vivo using cyanine–cojugated monoclonal antibodies", *Cancer Immunol Immunother* (1995) 41, pp. 257–263.

Weissleder, Ralph, et al., "In vivo imaging of tumors with protease–activated near–infrared fluorescent probes", *Nature Biotech*, vol. 17, Apr. 1999, pp. 375–378.

Hüber, Martina M., et al., "Fluorescently Detectable Magnetic Resonance Imaging Agents", *Am. Chem. Soc.* (1998), pp. 242–249.

Sweeney, Thomas J., et al., "Visualizing the kinetics of tumor–cell clearance in living animals", *Proc. Natl. Acad. Sci.* vol. 96, No. 21, Oct. 12, 1999, pp. 12044–12049.

* cited by examiner

*Primary Examiner*—Marvin M. Lateef
*Assistant Examiner*—Jeoyuh Lin
(74) *Attorney, Agent, or Firm*—Dorsey & Whitney LLP

(57) ABSTRACT

A method for detecting and localizing a target tissue within the body in the presence of ambient light in which an optical contrast agent is administered and allowed to become functionally localized within a contrast-labeled target tissue to be diagnosed. A light source is optically coupled to a tissue region potentially containing the contrast-labeled target tissue. A gated light detector is optically coupled to the tissue region and arranged to detect light substantially enriched in target signal as compared to ambient light, where the target signal is light that has passed into the contrast-labeled tissue region and been modified by the contrast agent. A computer receives signals from the detector, and passes these signals to memory for accumulation and storage, and to then to image processing engine for determination of the localization and distribution of the contrast agent. The computer also provides an output signal based upon the localization and distribution of the contrast agent, allowing trace amounts of the target tissue to be detected, located, or imaged. A system for carrying out the method is also described.

17 Claims, 16 Drawing Sheets

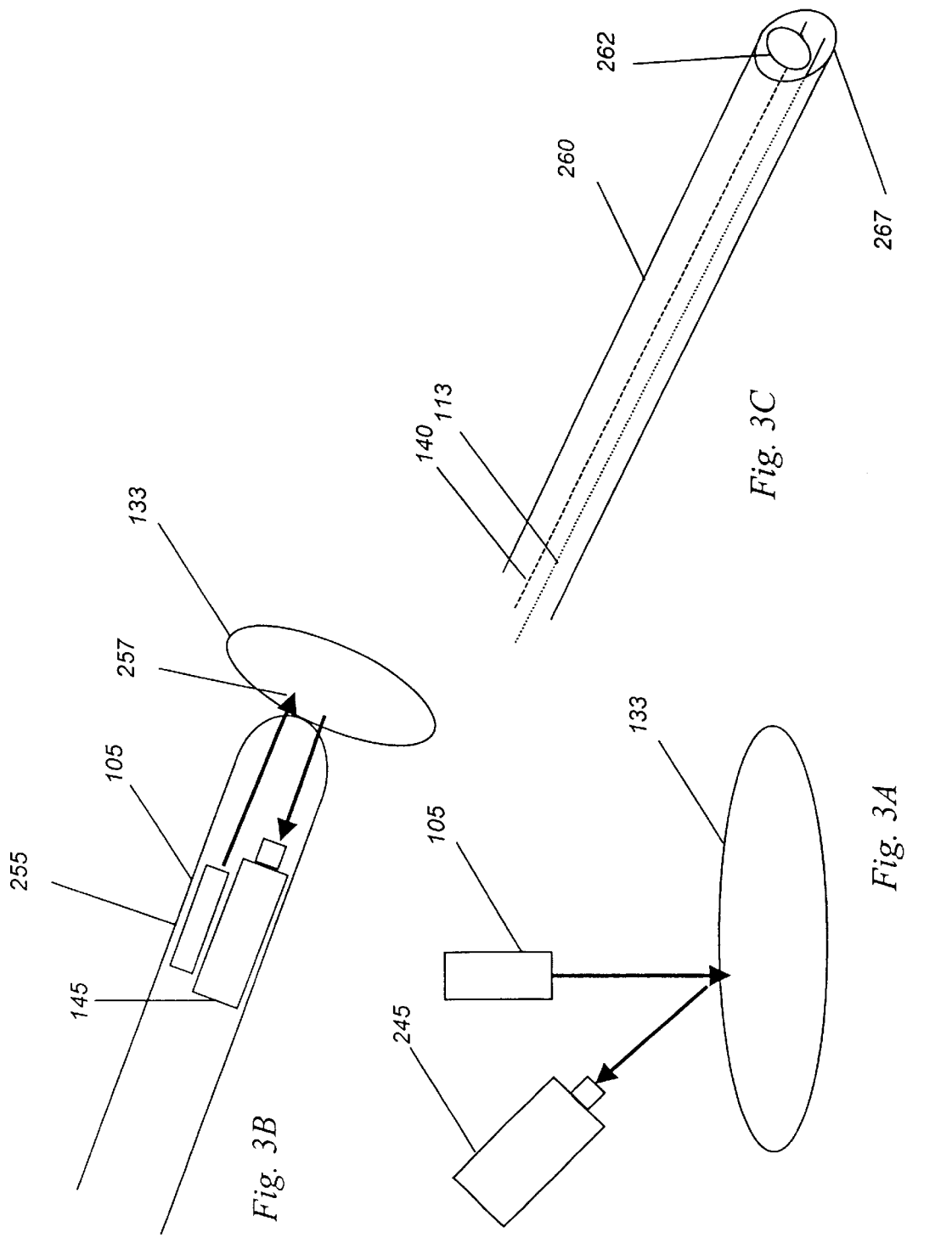

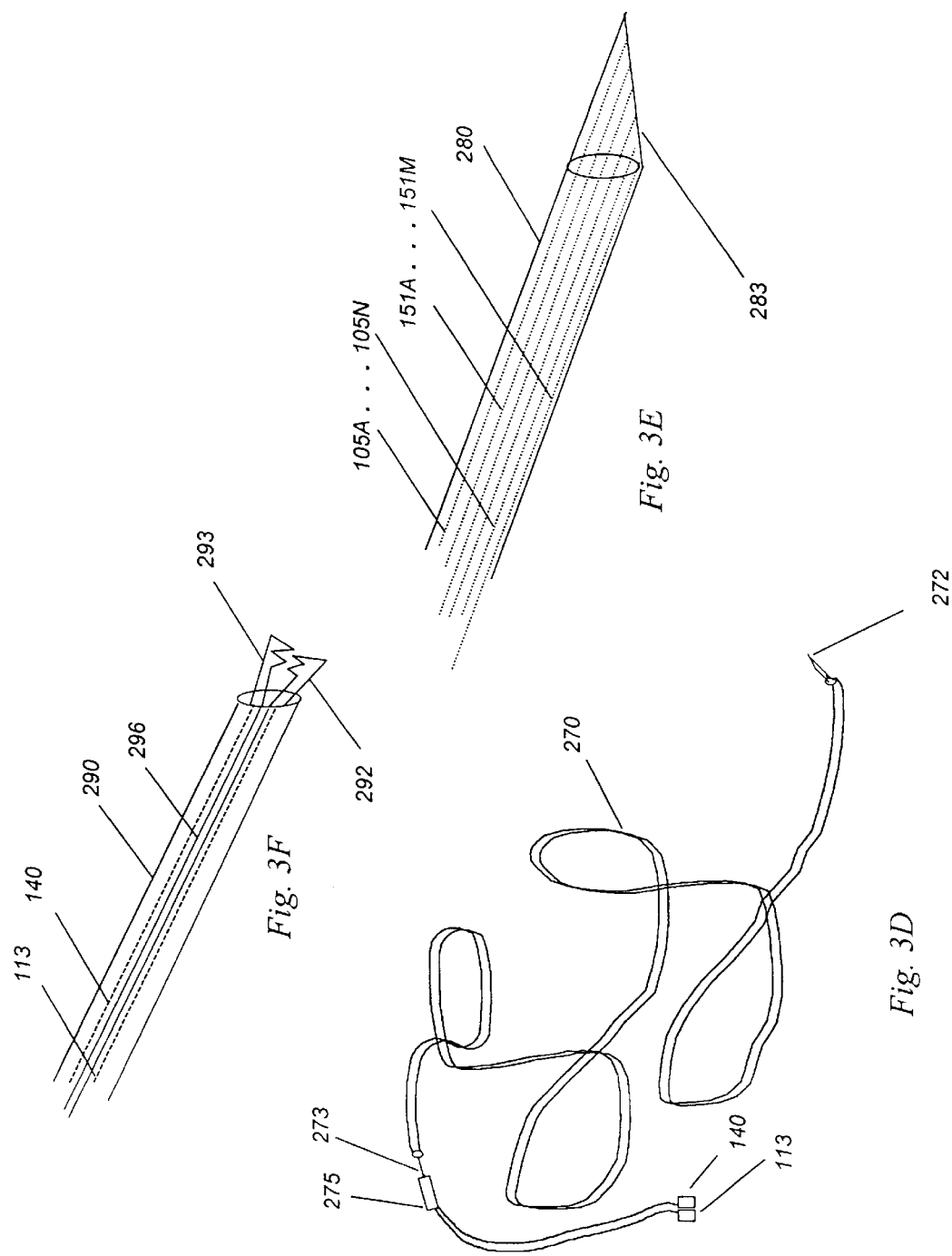

375

381

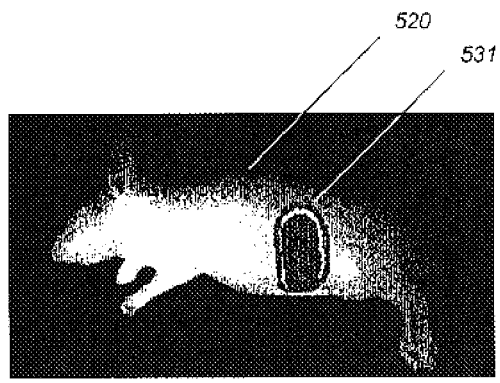 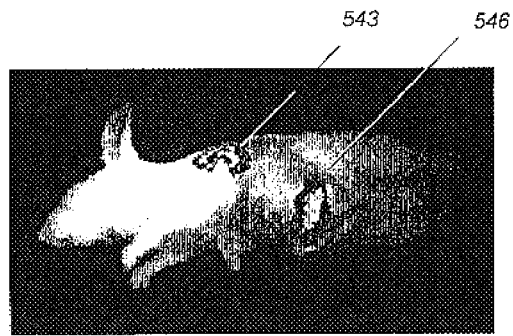
Fig. 9A                    Fig. 9B

OPTICAL IMAGING OF INDUCED SIGNALS IN VIVO UNDER AMBIENT LIGHT CONDITIONS

FIELD OF THE INVENTION

The present invention relates generally to systems and methods for using gated optical detectors in ambient light in order to determine the location or distribution of an induced optical signal in vivo, and more particularly relates to coupling the use of a gated intensified charge-coupled device imaging camera, insensitive to room light, to the use of a targeted fluorescent contrast agent and a synchronized illuminating laser to detect and image cancer cells present in the human body in trace amounts in vivo and in real time, during invasive cancer surgery or guided tumor biopsy, without requiring a darkened operating theater.

BACKGROUND OF THE INVENTION

Optical imaging systems and methods which provide real-time detection, diagnosis and imaging of diseases such as cancer are known in the art. The application of such systems in vivo during real time medical or surgical procedures has been limited by a poor signal to noise ratio. This low signal to noise ratio is a consequence of the low strength or absence of an optical signal arising from the target tissue, the high level of background noise from any ambient light, and the poor sensitivity and specificity of the detected optical signal.

The magnitude of the signal to noise problem is best appreciated by considering that the reflected irradiance from tissue surfaces in an operating room can be as high as 10 $mW/cm^2$, or more, under the brilliant surgical headlamps and overhead spotlights. Under normal operating room illumination, this translates into $10^{18}$ (1 billion billion) photons reflected from each square centimeter of tissue per second. In contrast, the native fluorescence may be on the order of $10^7$ below the incident light, about $10^9$ photons/$cm^2$/sec, or less. This makes the detection of trace amounts of disease difficult in ambient light. Using the photon counts in the example just described, the ambient light is one billion fold greater per square centimeter than the detectable native fluorescent signal from a 1 mm tumor, or one trillion fold greater per square centimeter than the signal from a 100 micron tumor. Complicating matters further, some target tissues or disease conditions have a signal that is non-specific, or may have no detectable optical signal at all.

Detection of trace amounts of target tissue in room light therefore requires that the signal to noise ratio be improved beyond what is currently taught in the art, in the range of $10^4$ to $10^9$ fold improvement, either by reducing the noise introduced by background ambient light, or by increasing the strength and specificity of the target signal, or both.

With regard to improving the signal to noise through the rejection of ambient light, the majority of known optical diagnostic systems and methods simply ignore, background subtract, or turn off room light. Examples include most invasive devices equipped with optics, such as catheters, needles, and trocars (e.g., U.S. Pat. No. 5,601,087), as well as noninvasive devices for imaging or measuring the optical features of living tissue externally (e.g., U.S. Pat. Nos. 5,936,731, WO 98/10698, Sweeny et al. in Proc. Natl. Acad. Sci. 1999;96(21):12044–12049, Weissleder et al. in Nature Biotech 1999;17:375–378). However, turning off the lights or obscuring a view of the patient using dark drapes during a medical procedure is disadvantageous and possibly dangerous, especially during critical surgical procedures. On the other hand, simply ignoring or background subtracting ambient light risks overflowing the detector and/or burying weak signals from trace amounts of tissue in the background noise. Thus, such simplistic approaches diminish the possibility of real-time feedback during medical procedures, unless the ambient light is specifically rejected.

Schemes for the true rejection of ambient light are known, and include the use of band pass filters, temporal signal modulation, and lifetime analysis. However, such methods often fail in ambient light. For example, a bandpass filter wide enough to pass the bulk of a biological fluorescent signal in vivo will still pass at least 5% of the ambient light as well, far short of the needed $10^4$ to $10^9$ enrichment in signal to noise required to unmask a weak native fluorescence. Temporal methods can be arranged to provide background rejection in tissue imaging, however approaches such as amplitude modulation (e.g., U.S. Pat. Nos. 5,213,105, 5,648,269, and 5,865,754) and time-of-flight measurement (e.g., U.S. Pat. No. 5,919,140, WO 98/10698) have historically been configured instead to measure temporal information about the time required for photons to traverse a tissue or leave a fluorescent molecule, rather than to reject ambient signal. In addition, such temporal schemes work well only when the target signal is sufficiently strong that a temporal response (time-of-flight rise or fall time, phase shift, fluorescence lifetime) can be accurately estimated, and thus fail to operate in real time when only trace amounts of the target tissue are present, or when the ambient light is strong.

All of the above systems and methods fail to reject significant amounts of background radiation, operate only under darkened conditions, require strong target signals, or require long integration times that preclude real-time use, and thus fail to reliably detect trace amounts of a target tissue in the presence of common levels of ambient light.

The above drawbacks notwithstanding, improved ambient light rejection alone may not be sufficient to achieve a real-time system for use in vivo under operating room conditions. Although some large cancers may be detectable using native signals (e.g., U.S. Pat. No. 5,647,368), many physiological and pathological conditions possess no detectable native optical signal, or have only a weak or non-specific optical signature, particularly when trace amounts of disease are to be detected.

Contrast agents have been used in the past for medical monitoring and imaging when the inherent or native signal in vivo is absent or poor. A contrast agent serves to lend a strong, identifiable signal to an otherwise poorly detectable tissue. In this regard, optical contrast agents are known in the art. The majority of known optical contrast agents are untargeted (e.g., U.S. Pat. Nos. 5,672,333, 5,928,627, WO 97/36619, Lam et al. in Chest 1990:97(2):333–337, and Huber et al. in *Bioconjugate Chem* 1998;9:242–249). Such untargeted agents rely largely upon the physical characteristics of the agent, such as solubility in fat versus water, or upon cellular metabolism, to non-specifically partition them into a particular tissue. As untargeted dyes produce widely distributed and nonspecific signals, they require a large stained tissue volume in order to generate a statistically clear signal in vivo, they tend to produce weak signals, insufficiently above background noise, from smaller or trace target tissue volumes. For example, photodynamic therapy agents accumulate in certain cancerous cells (Lam et al., Huber et al.), but they also accumulate in normal tissues. None of the preceding optical contrast methods or devices teach in vivo targeting of rare cells through the use of highly specific targeting agents, and thus will fail for use in the detection of trace amounts of a target tissue in vivo.

A few agents allowing for more localization targeting of dye are known. For instance, Sweeny et al. teach a process of genetically altering cells cultured or grown outside of the body, followed by insertion of these cells into the body for imaging. Such removal and reinsertion of cells may not make sense for use in patients with spontaneous diseases such as cancer, which should not be altered and reintroduced into the patient's body. Further, as the transformed cells glow continually, there is no inducible component to the light (such as fluorescent light induced using a flash lamp), and therefore little if any enhancement is possible through use of gated rejection of ambient light. Weissleder et al. (Nature Biotech 1999;17:375–378) teach another dye that is targeted in the sense that it is locally activated, while WO 98/48846 suggests multiple methods of creating optical dyes for use in vivo. Each of these approaches is realized without provision for the specific rejection of ambient light though use of a gated detector, and thus will fail for use in the detection of trace amounts of a target tissue in vivo and in the presence of ambient light.

In summary, none of the preceding approaches suggest gating the detector to substantially reject ambient light, nor do they suggest combining a gated ambient-light-insensitive imager, a high-power synchronized light source, and highly-specific tissue-targeted contrast agent into a cohesive system for detecting and imaging trace amounts of target tissue in room light. Therefore, device and methods taught in the present art will fail in many cases to detect and localize trace disease such as small primary cancers, early metastatic disease, local inflammatory conditions, or unstable coronary wall plaque, in vivo and in real time under ambient light conditions. A real-time optical system and method to detect or image an induced or contrast-influenced target tissue signal in vivo and in ambient light has not been taught, nor has such a tool been successfully commercialized.

What is needed, and not yet suggested or taught, is a method and optical system to detect a signal from trace tissue in vivo and in real time despite the presence of a high level of ambient light, possibly including the step of enhancing a weak native signal (or creating one where one did not previously exist), in order to produce an optical system for detecting, imaging, targeting, and treating of tissue, such as trace amounts of cancer, in vivo and in real time.

SUMMARY AND OBJECTS OF THE INVENTION

The present invention relies upon gating an optical detector or optical imaging camera so as to allow for rapid detection, imaging, localization, or targeting of trace amounts of target tissue in vivo and in real time in the presence of ambient light, with or without the presence of a targeted optical contrast agent.

A salient feature of the present invention is a recognition that ambient light can be substantially rejected ($>10^4$ rejection) by gating the detection or imaging system to be sensitive to light arriving only during specific brief intervals, and that if a native or contrast-influenced target signal is produced with greater intensity during these brief intervals, then such ambient light rejection results in an reduction in the background signal and a relative enrichment of target signal with respect to the ambient light noise.

Another salient feature is that a weak or absent target signal can be enhanced in intensity, specificity, or both through use of a targeted contrast agent, and that optical systems and methods can be used to induce and detect this enhanced contrast signal in synchrony with gated detection, thus again enabling improved real-time detection or imaging during targeted medical procedures and therapies.

Accordingly, an object of the present invention is to provide a system and method to detect, localize, image, or target a selected tissue using optical detection or imaging in ambient light, wherein use of conventional ungated detectors would otherwise have required highly darkened rooms, unacceptably long integration times, or extensive averaging and background subtraction.

Another object is to substantially reject the background ambient light ($>10^4$ rejection), while relatively preserving the target signal, such that the resulting detected light is enriched in target signal with respect to the reduced background light noise.

Another object is that the illumination source may be synchronized with the detector gating, allowing for a high peak illumination power using brief periods of illumination, and resulting in strong induced target signals using a low average illumination power.

Another object is that trace amounts of tissue, such as cancer, vascular disease, neovasculature due to angiogenesis, and infection, can be detected and imaged in real time with a high sensitivity. In some embodiments of the present invention, it may be possible to detect as few as 100 cells or less, in vivo and in real time.

Another object is that a weak or absent tissue signal may optionally be enhanced by use of a targeted optical contrast agent, and that this targeted agent can be induced and detected in conjunction with detector gating, resulting in an improved target tissue signal with respect to background noise. Such optical contrast can be an endogenous tissue component, or can be an exogenous optical contrast agent administered to the subject, followed by a period to allow distribution and localization sufficient for detection or imaging. The contrast agent may be administered in an active form, or as a pre-active pro-drug that requires metabolic activation. The contrast is ideally targeted via a targeting moiety, such as an antibody, antibody fragment, protein or synthetic peptide, or receptor analog, or the contrast may be locally activated or altered via a metabolic processing step, such that the majority of the signal arises from the target tissue with minimal or no enhancement of the surrounding tissues.

Another object is that by combining an ambient-light-insensitive detector or camera, an exogenous targeted contrast agent, and a synchronized illumination source, sufficient enhancement in the target tissue specific signal as compared to the ambient light background signal may occur so as to allow the detected optical signal to reach medical relevance.

Another object is that the targeting moiety of the contrast agent can be altered or changed during manufacture of the agent, such that the specificity and target tissue of the contrast agent can be selected from a menu of many different target tissues, while retaining a substantially similar imaging platform system.

Another object is that the dye moiety of the contrast agent can be altered or changed during manufacture of the agent, such that the wavelength and optical characteristics of the contrast agent can be altered while retaining a substantially similar target tissue and target tissue sensitivity.

Another object is that the detection, localization, or imaging of the target signal can be used to provide feedback during an invasive procedure, to provide control for any process of collection or treatment, such as an ablation process.

Another object is that this monitoring may represent a decision point upon which a human response may be initiated, such as with a visual guidance display or an alarm bell that signals correct placement, or an interlock decision may be initiated when a treatment is complete, such as via an output signal attached to a medical device.

Another object is that localization of an invasive medical instrument with respect to a target tissue can be made. This localization can be in the form of a determination of the distance or direction of the device to the target tissue, or the instrument can be localized in space in one or more dimensions. Such information can be used to make a guidance signal for the purpose of guiding the medical instrument to a target location. Alternatively, the localization can be in the form of a determination of the tissue compartment in which the device is currently placed, such as tumor, normal prostate, residual prostate cells outside of the prostatic capsule, or by tissue type, such as skin, muscle, or blood vessel.

Another object is that system and method can be enhanced by concurrent or a priori knowledge, such as the known optical spectral characteristics of target tissues or tissues expected to be encountered during placement (which can be stored for reference in the device or in the instrument), the area of the body the physician is working (such that far away tissues need not be considered in the analysis), or information from other medical scans (such as a CT or MRI scan). This optical approach may be combined with other real-time approaches, such as a combination of an ultrasound probe and an optical instrument to produce an overlay of an optical image upon a standard ultrasound image. Such a combination would provide both structural (ultrasound) and biochemical (optical) images simultaneously.

Another object is that the detection, localization, or imaging information can be presented to the user in a number of ways, such as an image processed for ease of interpretation, a displayed word describing progress, a variable alarm to indicate the progress of treatment of a tumor through changes in pitch or speed or intensity of the tones, or other manners of presentation, in such a way as to allow the user to gain an incremental understanding of the progress of the procedure or therapy.

Another object is that detection system can be used in animal research to provide noninvasive monitoring of physiologic, pathologic, or pharmaceutical processes, such as tumor growth under treatment by chemotherapeutic agent, with one or more of the following goals: reducing animal usage, improving data quality, shortening test cycles, reducing costs of development, collecting data for FDA or quality control purposes, and/or for research and testing of pharmaceuticals.

A final object is that the detection or imaging system is sufficiently sensitive that embodiments within the spirit of the invention can be used for relatively longer integration times to detect disease buried deep within the human body, at a possible cost of losing real time feedback, in cases where conventional monitoring or imaging systems may lack the specificity, such as bone scans and screening of deep scar tissues for sites of cancer recurrence.

The systems and methods as described have multiple advantages. One advantage is that the system can be used in room light during surgery, in vivo and in real time. Another advantage is the production of images in real-time, even for tissues that are present in trace amounts. Another advantage is that the system as described is a platform system, with the target tissue changeable at the time of manufacture of the contrast agent. Another advantage is that the system may allow reduction of animal use or length of studies in animal research. A final advantage is that the system, by virtue of a high specificity, may have application to use in vivo for the detection of deeply buried processes, though integration times may be long and the real time aspect of the present invention may be lost.

There is provided a system for monitoring or imaging optical characteristics of tissue in the presence of ambient light, with or without the presence of a signal-enhancing targeted optical contrast agent. In one example, the system has a gated digital imaging camera, optically coupled to the tissue through lenses and filters, placed above the operating field, and a laser light source that illuminates the tissue and which is synchronized with the gated camera. The camera detects a portion of the laser light that has passed through the tissue and interacted with a contrast agent in vivo. Use of a contrast agent improves the sensitivity of the system by enhancing a weak or absent signal from the target tissue. The gated detector enhances the sensitivity of the system by rejecting a significant fraction of the background ambient light, while preserving signal from the contrast agent. A computer controls the light source and gated camera, and receives a signal from the gated detector, which may be stored in memory. An image processor receives a signal representing raw data from the computer and provides a contrast localization image, used to identify and image a target tissue, to target a medical instrument or therapy toward a particular site in the body, to determine the accuracy of placement of an invasive instrument, or to provide a feedback signal to the user regarding therapy progress. A method of imaging a contrast agent in tissue in the presence of ambient light is also described.

The breadth of uses and advantages of the present invention are best understood by example, and by a detailed explanation of the workings of a constructed apparatus, now in operation and tested in model systems, tissue culture, and in animals, and humans. These and other advantages of the invention will become apparent when viewed in light of the accompanying drawings, examples, and detailed description.

BRIEF DESCRIPTION OF THE DRAWINGS

The following drawings are provided:

FIGS. 3A–3F show several possible configurations of light source and detector.

FIGS. 9A–B show noninvasive and invasive overlay images, respectively, of dye in the abdomen of a mouse.

DEFINITIONS

Figure 1:
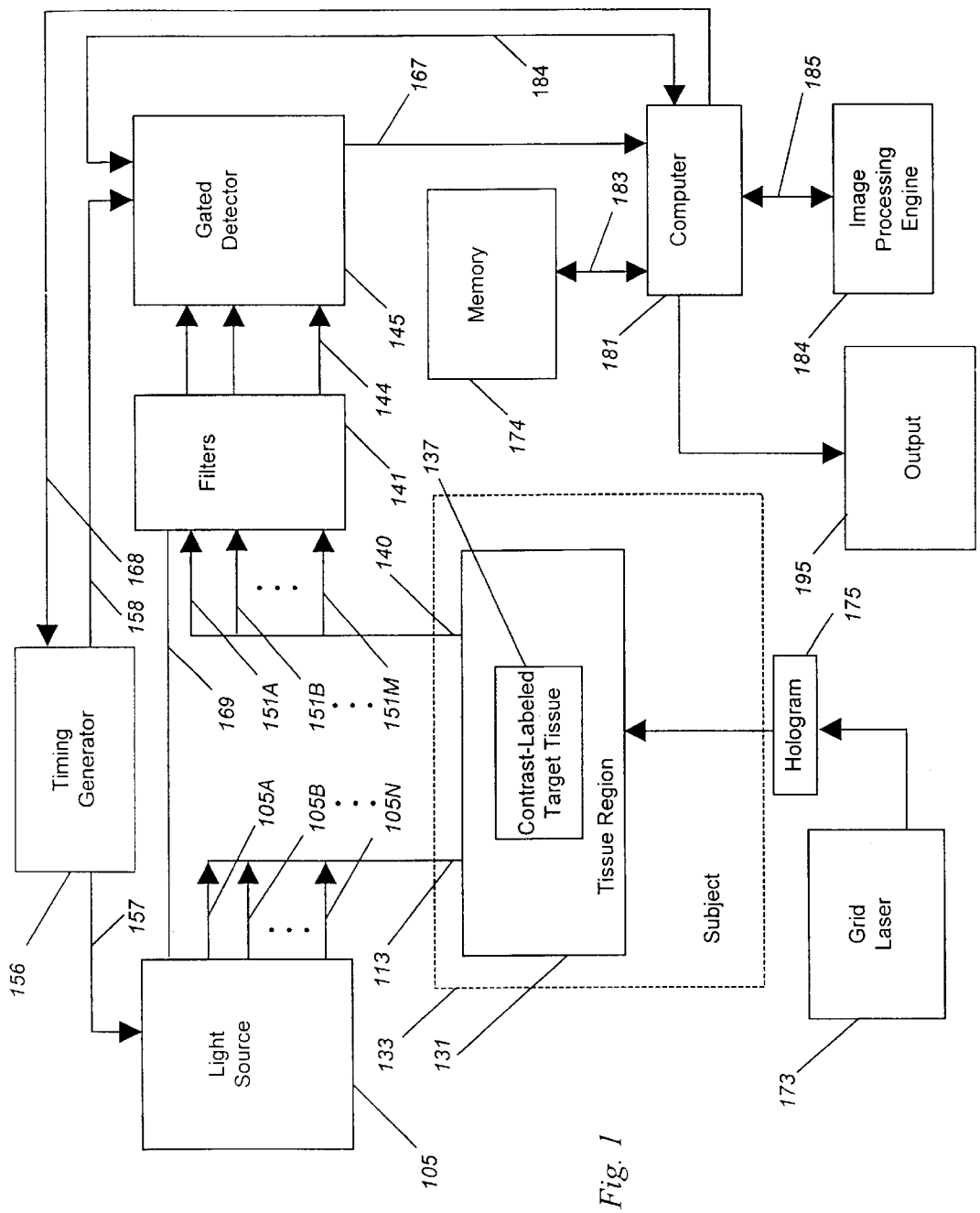
FIG. 1 is a schematic diagram of a system coupling a gated imaging device to use of a targeted contrast agent in accordance with the invention.

For the purposes of this invention, the following definitions are provided:

Real Time: A measurement performed in 10 seconds or less, and preferably under 1 second, that allows a procedure or a treatment plan to be modified based upon the results of the measurement.

Subject: A living animal, plant, viral, or bacterial subject, with an emphasis on mammals, especially humans.

In Vivo: A measurement performed on tissues within a living subject.

Target Tissue: A tissue or cell type to be detected or imaged. For prostate surgery, a target tissue may be residual prostate cells beyond the surgical margin; for breast surgery, a target tissue may be any breast tissue present in the lymph node bed.

Target Tissue Signal: An optical signal specific to the target tissue. This signal may be enhanced through use of a targeted contrast agent.

Ambient Light: The background light incident upon a subject. For a subject on the operating room table, the ambient light includes at least room light, and may include overhead lamps, the surgeons' headband-based lamps, and other light sources. Internally, ambient light can include light from an endoscope.

Signal to Noise: The ratio of the strength of a target signal to the background noise. This can be increased either by improving the target signal, or by reducing the background noise. In this invention, the primary source of background noise is the ambient light, but other sources include non-specific binding of the contrast agent, shot noise in the detector, autofluorescence, and other effects, unless such noise sources are used as a source of contrast.

Induced Signal: A signal induced by exposure of the subject to illumination by a source of electromagnetic radiation, and is a direct result of the interaction of that radiation with an endogenous or exogenous source of contrast. This includes the absorbence of light by a dye, the fluorescence or phosphorescence of a biomolecule in response to excitation light, or even the emission of light from an internal reporter in response to an external electromagnetic field. An example of a non-induced signal is a luciferase-based process, such as that in the firefly, in which the energy for the glow is based upon a biological energy source (bioluminescence) rather than in response to a radiation source.

Contrast: An identifiable and measurable signal, either an endogenous component of the tissue or an exogenously agent, that can be differentiated from the background signal.

Optical Contrast Agent: An agent that interacts with and modifies optical illuminating radiation, and provides a measurable contrast signal. Ideally, the contrast agent provides a differential contrast for the target tissue site versus other tissues. The agent may require bioactivation or bioinactivation in order to achieve this differential contrast, and this differential contrast may be more or less depending upon route of administration, dose, and time delay between administration and imaging.

Optical Emitting Reporter: An agent that spontaneously emits light without external energy sources, such as the bioluminescent protein luciferase when coupled to the proper substrates. A bioluminescent molecule stimulated to emit light in direct response to illumination with a light source is operating as an optical contrast agent, not an emitting reporter.

Targeted Optical Contrast: An optical contrast agent that is preferentially guided to a target tissue via a targeting moiety. The targeting moiety can be an antibody, a receptor analog, a protein or synthetic peptide of at least two amino acids, an antibody fragment, or other targeting moieties known in the art.

Substantial Enrichment: A signal to noise enrichment after ambient light rejection and/or contrast enhancement that allows detection or imaging to reach medical relevance. For operating room procedures, this preferentially occurs in real time, and likely requires a minimum ambient light rejection and improvement of signal to noise of $10^4$. Typically, this is expected to require a $10^6$ to $10^8$ signal to noise improvement.

Surgical Instrument: A device used primarily to cut or remove tissue, or to reattach tissue, in the performance of surgery.

Imaging Device: A device that provides a medical image. An imaging camera that resides over the bedside during surgery, or a hand held imaging probe, are imaging or devices, not surgical instruments.

Light: Electromagnetic radiation from ultraviolet to infrared, namely with wavelengths between 10 nm and 100 microns, but especially those wavelengths between 200 nm and 2 microns.

Light Source: A source of light. It may be composed of a simple light bulb, a laser, a flash lamp, or another light source or combination of sources, or it may be a complex form including gateable or triggerable electronics, a light source, a filter element, a transmission element such as an optical fiber, a guidance element such as a reflective prism, and other elements intended to enhance the optical coupling of the light from the emitter to the skin or tissue under study. The light source may be continuous, pulsed, or even analyzed as time, frequency, or spatially resolved. The emitter may consist of a single or multiple light emitting elements.

Light Detector: A detector that generates a measurable signal in response to the light incident on the detector. As above, it may be single or multiple, simple or complex. Light detection may be performed in reflectance, in transmission, or in a tomographic fashion. The collected light may be light that has been influenced by transmission, absorbence, scattering, fluorescence, phosphorescence, or other optical interactions of the illuminating radiation with a contrast agent. Detection may include time, frequency, or spatially resolved measures.

Gated Detector: A light detector arranged to allow light collection to be gated, that is: turned rapidly on and off. In an ambient-light-insensitive gated system, the primary function of the gate is to reject ambient light. Ambient light rejection occurs as a function of the off-time to on-time gating ratio. Such gating can occur at speeds of 1 KHz to over 1 MHz. Examples include a gated intensified CCD (ICCD) camera and an avalanche photodiode arranged to be sensitive or insensitive to incident photons depending on an input gate voltage.

Optical Coupling: The arrangement of a light source (or light detector) in such a way that light from the source (or detector) is transmitted to (or detected from) tissue, allowing passage through the tissue and possible interaction with a contrast agent. This may require the use of optical elements such as lenses, filters, fused fiber expanders, collimators, concentrators, collectors, optical fibers, prisms, mirrors, or mirrored surfaces.

Description of a Preferred Embodiment

One embodiment of the system and method of the present invention will now be described. The system has been tested and has provided the examples that follow the description of the one embodiment.

In the device or system shown in FIG. 1, light is emitted by high intensity pulsed light source 105 (in this case, a 742 nm pulsed laser, model LDX-3115-740-HHL, LDX Optronics, Maryville, Tenn.). Source 105 has embedded beam-shaping optics (various cylindrical shaping lenses, Edmund Scientific, Barrington, N.J.) to pass light through optical coupler 113 and illuminate tissue region 131 of subject 133 using light from coupler 113. Coupler 113 can be an optical fiber, or can be airspace between illumination source 105 and tissue region 131. Region 131 contains cells of target tissue 137. Target tissue 137 is labeled with an optical contrast agent, distributed throughout region 137 and shown fluorescing in image 194 in FIG. 2. With regard again to FIG. 1, gated detector 145 (Gen-4 gated ICCD Camera, I-max 612/D model, Roper Scientific, Trenton N.J.) receives modified light 144 from subject 133 after passage of modified light through optical coupler 140 and through high-efficiency bandpass filter 141. Filter 141 allows laser light to be substantially blocked ($\sim 10^6$–$10^8$), and allows the majority of room light to be blocked as well (>95%). Optionally, filter 141 may be configured using N filters, any one of which may be placed in front of detector 145 to produce sensitivity to multiple dyes or sensitivity to depth of dye emission within tissue region 131.

Both detector 145 and source 105 are coupled to timing generator 156 under the control of computer 181 via cables 157, 158, and 168. Computer 181 triggers detector 145 to collect light only when the light source has induced a signal in the subject, thus allowing for high laser power to be used on an infrequent basis. This accomplishes two goals. First, the integrated period of measurement is short, thus excluding the majority of ambient light. Second, the intensity of the weak induced signal is maximized, thus improving the strength of the signal. The triggering of detector 145 by computer 181 may be synchronous with illumination provided by source 105, or may be delayed slightly to take advantage of signal decay kinetics for an improved signal.

Alternatively, source 105 may be a very bright light source, such as an Alexandrite laser (LAI-101 model, Light Age, Somerset N.J.), which would have sufficient power to allow data to be collected in nanoseconds, with very low ambient light background secondary to the short measurement times. Source 105 may also be comprised of N multiple sources 105A–105N (such as different diodes of various wavelengths), fiber-coupled or lens-coupled (rather than free-space), collinear with the detector, or other modifications that are standard in the art. Optional reference fiber 169, bypasses the tissue or sample for use in monitoring the optical characteristics of source 105. Similarly, detector 145 may be M multiple detector paths 151A–151M.

A target grid can be projected onto the tissue field using grid laser 173. Light from laser 173 passes through holographic filter 175 to create a grid that will be visible to the surgeon, as well as visible in the image when grid laser 173 is on. This grid provides a method to visually co-register what the user sees on the tissue with what is seen in any image displayed to the user. Such an orienting grid may be essential for a surgeon to respond in real-time to the image presented on the output device, such as on a video screen.

Unprocessed (raw) images from detector 145 are downloaded under control of computer 181 via link 167, and stored in memory 174 via cable 183. Multiple raw images can be stored in memory 174, allowing for later integration, averaging, background subtraction, edge detection and sharpening, and other techniques for correction of the images for instrument response or improved display. Memory 174 also allows for multiple regions of the tissue to be imaged and later compared. Each raw image is passed to contrast image processing engine 184 via links 183 and 185, under the control of computer 181, where the raw images are processed, analyzed, and combined to yield an output that is a measure of the distribution and localization of a contrast agent.

A discussion of processing engine 184 now follows. The determination of the localization and distribution of contrast agent 141 by engine 184 is performed by a computer, constructed with analysis routines, and arranged so as to provide a measure of the localization and distribution of a contrast agent based upon collected data. However, engine 184 could also be a calculator or other device configured so as to provide tissue or contrast location output. As noted above, computer 181 may be a different computer than that used in engine 184, or the same computer may be used for both functions. In this preferred embodiment, processing engine 184 is a computer configured so as to perform two functions: image processing and statistical analysis.

With regard to image processing, engine 184 collects a) an image of tissue region 131 as it appears to the user in room light, termed the subject image, b) a gated image of region 131 with source laser 105 on, termed the illumination image, and c) a gated image of region 131 with source laser 105 off, termed the background image. The subject image is used to help orient the user as to the location of the tissue tested, and to identify the location of any identified target tissue, while the background image is used to correct the illumination image for background signal in the absence of light from source 105, in order to produce a background-corrected tissue image, termed the background-corrected sample image. By subtracting at each pixel the value of the background image from each pixel in the illumination image, engine 184 generates a contrast map. Each of the illumination and background images can be integrated, smoothed, averaged, or accumulated by engine 184 using approaches known in the art. Alternatively, or in addition, repetitive subject and sample images can be collected and integrated on the CCD chip itself during multiple gating and laser illumination periods. This reduces the relative size of the read noise from the ICCD, and was used in Example 2 through Example 5. If separate images are collected with each pulse, the summation of these images can be performed mathematically by engine 184 during multiple collection periods and multiple laser pulses. Collection of the sample and background images may be occur sequentially, or multiple samples may be interleaved for averaging with the laser alternately on and off with each successive image collection. Standard image processing approaches can be added to the processing approach, such as edge detection, image sharpening, or flat-field correction (the latter used to reduce the effect of uneven illumination and reflection). For example, the images may be clipped at an adjustable multiple of the image standard deviation, to remove the majority of random noise in the image.

Figure 2:
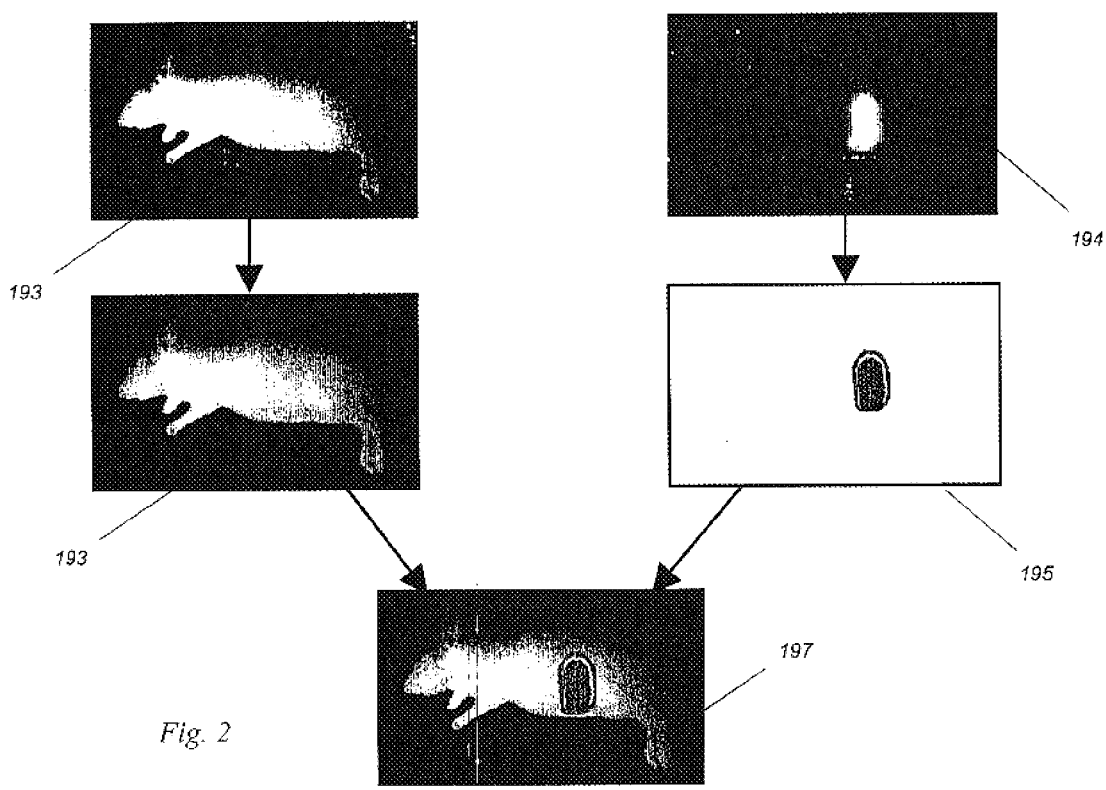
FIG. 2 shows a subject image, a contrast map, and a fused image as displayed to the user by the system shown in FIG. 1.

As shown in FIG. 2, engine 184 next takes a colorized background-corrected tissue image, and the gray scale room-light subject image, and fuses these two images into a single image. To accomplish this, subject image 191 is scaled for optimum contrast, and converted into gray-scale image 193. Background-corrected tissue image 194 is converted to false color image 195, after processing and scaling. When images 193 and 195 are fused, resulting display image 197 shows a black and white view of the patient (with a visible grid if grid laser 173 had been used during collection of the subject image), overlaid by a color tissue image indicating the location, depth, and/or cell number of the target tissue. The color in image 197 may be qualitative, such as indicating collections of cells with more than 100 cancer cells per $cm^2$, or quantitative, such as indicating the number of cancer cells per $cm^2$ or the mean depth of the target signal for that particular pixel.

Optionally, engine 184 may use spectroscopic signals from the contrast agent in order to determine signal depth, as discussed later in Example 10. This is possible as tissue scatters different wavelengths of light in an unequal manner. Engine 184 may also use spectroscopic signals from a contrast agent or native signals from nearby tissues to identify tissues by type, and methods of doing this are known in the art.

In order for engine 184 to correct for any gradients or hot spots in source 105, an image of just the illumination from the laser can then be collected prior to surgery to produce an illumination distribution image, corrected for background as previously described. Alternatively, a reflected intensity at a preselected wavelength may be used to create a reflectivity image. Then, each intensity point in the background-corrected tissue image can be divided by the corresponding intensity point in the background-corrected illumination distribution image, to produce an illumination-corrected tissue image.

With regard to statistical processing, engine 184 performs the statistical processing steps necessary to identify the location, presence, number, depth, and image of an induced signal, such as that produced by a targeted contrast agent located in tissue region 131, if any. Statistics calculated for the illumination, background, and background-correct tissue, and contrast images include mean values, standard deviations, statistical significance of detected signal, signal to noise enhancement, tumor volume, and the like. Clipping at a specified upper limit for the noise in the final image allows small cancers to be seen, as shown in Example 4.

Contrast localization may be improved by using a computational comparison to a set of reference criteria (spectra or features of the spectra such as intensity of fluorescence at one or more wavelengths, ratios of intensity at two or more wavelengths, the first differential of the spectrum, or threshold values upon which to make classification decisions) in order to arrive at a determination. Such reference values may be updated over time as better understanding of the meaning of the spectra is reached, and may even be built into the sensor itself, such that each sensor comes calibrated for a certain tissue set or for a certain diagnostic procedure. One method of incorporating these reference values into the sensor would be the inclusion of a read-only memory (ROM) chip within the circuitry of the imaging device. Similarly, identification could be improved by background correction and correction for the instrument response function, as is well known in the art. The known approaches for fluorescent measurement and spectral analysis fall within the scope of the present invention whenever they are used to determine a measure of the location and distribution of a targeted contrast agent in vivo in ambient light, particularly when used to determine the location of a tumor within a scattering medium such as human tissue. Such targeting and localization may also include methods to allow for a chemical, physical, or receptor based analysis of the tissue, allowing resolution of the optical data into concentrations of hemoglobin, water, fat, etc. Such identifications may be used to identify tissues in the body, such as cancer, nerve, artery, vein, lymph node, white blood cells, and muscle.

Additionally, contrast engine 184 may be configured so as to be able to detect more than one contrast agent in use at a given time, and therefore multiple contrast agents may be used, such as in double or triple labeling studies, as shown in Example 9. In such cases, the target may be tissue that displays a simultaneous presence of more than one targeted feature, or simply display one targeted feature and not the other. Single or multiple contrast agents can also be used to measure the depth of the signal as well, as shown in Example 10.

The result of the image analysis is passed to computer 181, which generates output 195 in response. Output 195 is now more fully discussed. The output is a preprocessed signal that allows the user to obtain information regarding the distribution and localization of the contrast agent. In a preferred embodiment, the output is a fused image consisting of a black and white room light image of the tissue combined with a color overlay indicating the presence, location, extent, and/or depth of a target tissue. This display may indicate the location, distribution, and depth of a target tissue, and the relative location of any nearby surgical instrument with respect to that target tissue, either in absolute terms (e.g., accurately placed or not) or in relative terms (distance and angle from tissue to be treated. The result of this calculation, which is a measure of the distribution and localization of the contrast agent based upon the detected signal, is output 195.

In this description of a preferred embodiment, computer 181 fuses the subject image and the contrast map to produce a display image that will be shown to the user. However, this result may be a diagnostic classification (such as the presence or absence of a specific contrast agent or target tissue as shown in Example 1), a table (such as peak target intensity, mean target intensity, background noise, signal to noise, p-value of the detected signal, or the presence of one or more contrast agents or target tissues as shown in Examples 2, 3, and 9), a graph (such as the presence or absence of a contrast agent or target tissues over time or distance as shown in Examples 1 and 2), a number (such as the distance to a contrast agent or target tissue, or a peak contrast intensity, as shown in Examples 1 and 2), an image (such as the location, distribution, a depth of a contrast agent, a target tissue such as a sentinel node, as shown in Examples 1 through 5), a feedback signal to indicate that a procedure is complete, or an interlock to stop the action of a tool.

Operation of the System is Now Described

Approximately 7 days before a scheduled procedure or therapy, subject 133 receives an intravenous injection of antibody-targeted contrast agent. This time lag between injection and imaging can be substantially shorter (minutes to hours) when a small molecule such as a octopeptide is used, and may also be shorter when the dye requires local activation, thus rendering circulating contrast that has not reached the target tissue undetectable to the system. Whichever type of targeting molecule is used, the contrast agent is selected so as to provide a measurable contrast for a desired target cell in vivo. In this embodiment, the dye is a fluorescent molecule, Cy 7 (Nycomed-Amersham, Buckinghamshire, England) that is covalently coupled to an antibody. In the period following the injection but prior to imaging, the contrast agent has sufficient time to reach sufficient distribution and localization within the body by concentrating at the target tissue, and to be metabolized or excreted elsewhere. In this manner, the contrast agent provides a differential contrast for the target tissue site versus other tissues, and has enhanced the signal from the target tissue.

Once subject 131 is on the operating table, the imaging system as described is switched on. At the start of image collection, source 105 remains off. Grid laser 173 is turned on to project a target grid that will be visible in the initial subject image. A long integration time is used to collect the subject image using ambient light. Alternatively, the grid image and the subject image may be collected separately, and later fused into a single subject image. This subject image is stored in memory 174 by computer 181. Later this image of the subject and grid will be retrieved and displayed in black and white, with a color overlay of the contrast map indicating the location, depth, and/or cell number of any target tissue identified.

Next, computer 181 triggers light from source 105 to illuminate tissue region 131 in subject 133. Laser source 105 is pulsed on for 100 ns. At substantially the same time, detector 145 is also gated on for 100 ns, allowing the camera to collect the resulting induced signal in a synchronous manner with the illumination of tissue 131 by source 105. In this example, the triggering of source 105 and detector 145 is virtually simultaneous; however with some embodiments, the gating of detector 145 may need to be offset in timing, or turned on for a different length of time, than source 105 in order to maximize target signal and/or reduce background noise. An image is accumulated, termed the sample image, and is stored in memory 174 by computer 181.

Next, a third image is collected with grid laser 173 off and laser source 105 off, termed the background image. For this image, source 105 remains off while detector 145 is gated on for 100 ns, allowing gated detector 145, in this case a camera, to collect a background image from region 131 using a timing similar to that used during collection the of the subject image. The background image is accumulated, stored in memory 174 by computer 181, and is later used to produce a background-corrected sample image. Alternatively, the background light may be so low that collection of the background image, and the background correction of the sample image, may be safely omitted.

The subject image, with or without a grid visible, and the sample image, with or without background correction, are then fused as previously described to produce a black and white image of the subject with a color overlay indicating the presence, location, cell count, and/or depth of the target tissue, if any. This fused contrast map is sent to computer 181 for display on output 195.

This example illustrates use of a fluorescent contrast agent. However, other features can be used to derive the location of the contrast labeled tissue 137. For example, the contrast agent may be an absorbing dye, light source 105 could be a broad spectrum source emitting at multiple wavelengths, while gated detector 145 may be configured to be sensitive to the spectral distribution of the returning light. An example of depth determination of a dye is shown in Example 10. Techniques for such spectrally-resolved detection are known, and include standard spectrophotometry, hyperspectral imaging, time-resolved spectroscopy, frequency-domain spectroscopy, fluorescence lifetime, and other measures. Measured features can be any optical measurement, such as intensity, wavelength, time-course, mean optical path, frequency shift, polarization, and optical rotation. Provided such measures are coupled for use on or in opaque or scattering tissues, and are coupled to the use of an gated imaging system for the purpose of rejecting ambient light, such alternative measures are within the spirit of the present invention.

As noted above, a detection system may be noninvasive or invasive, and may be incorporated into a medical device. An example of a noninvasive detector is a camera constructed to image from above the surface of the tissue, rather than penetrating the surface of the tissue. In this case, both detector 145 and laser 105 may be placed at a distance from subject 133, and an image reconstructed using imaging algorithms described earlier, as shown where detector 145 is imaging camera 245, as shown in FIG. 3A. Alternatively, laser 105 or detector 145, or both, can be assembled into a medical or surgical probe, such as probe 255 being placed in contact with tissue surface 257 of tissue region 133, as shown in FIG. 3B. An example of an invasive detector would be if emitting elements, detecting elements, or both, are incorporated into a medical probe, needle, or catheter, which is then used internally within the body. In such cases, it may be essential to have the fibers stabilized with respect to the tissue, to assist in measurement reproducibility. Examples of invasive systems are needle 260 with emitter fiber as coupler 113, detector fiber as coupler 140, injection port 262, and cutting edge 267, as shown in FIG. 3C. Catheter 270 as shown in FIG. 3D, with extendable needle 272 controlled by wire 273, syringe attachment port 275, and with emitter fiber 113 and detector fiber as coupler 140 embedded into the needle (in a manner similar to that shown for needle 260). Scalpel 280 with multiple emitter fibers 105A to 105N and multiple detector fibers 151A to 151M embedded into cutting edge 283 of scalpel 280 to allow for imaging, is shown in FIG. 3E. Nibbler 290 with emitter fiber as coupler 113 and detector fiber as coupler 140 embedded into jaws 292 and 293, respectively, for simultaneously monitoring and removing contrast-labeled tissue, is shown in FIG. 3F. Such multiple emitter and detector fibers can be bundled to produce an optical imaging element that couples imaging camera 245 in FIG. 3A directly to the tissue, allowing much higher coupling efficiency that is achievable using a lens at a distance. An external imager would find utility in monitoring ongoing open-surgical procedures in real time, while an external surface probe would find use, for example, just prior to lymph node resection, to help identify the site of an initial incision, resulting in a smaller scar and less morbidity. Last, an internal needle or catheter could provide feedback to invasive or minimally invasive tools used to locate and treat a condition.

The detector, the light source, or both may be operationally coupled to an invasive instrument to provide ongoing tissue measurement, and feedback or interlock control based on output 195. For example, a needle probe may be designed to measure tissue, and inject a therapeutic substances when the correct tissue is identified based upon feedback from the contrast detection or imaging device, such as a needle 260 (FIG. 3C) that monitors tissue until it reaches the correct location for injection, as indicated by a rise in the contrast signal beyond a calculated or absolute threshold level, or nibbler 290 (FIG. 3F) that nibbles away at and removes a tumor until the contrast signal remaining within the tissue disappears. Nibbling probe 290 removes tissue using morselating jaws, with washing and suction channel 296 surrounding jaws 292 and 293. If tissue is identified as containing contrast, the tissue is removed in small morselated pieces. In this way, the margins of resection may be made clear of disease, while sparing the normal tissue as much as is safe. This may allow for minimally invasive surgical procedures based upon optical contrast guidance. For example, a breast probe may be used to nibble out a breast tumor through a small hole, turning an invasive procedure into a minimally invasive lumpectomy. Alternatively, jaws 292 and 293 can be replaced with other tissue removing mechanisms, such as ablation fibers, tissue homogenizers, or other approaches. Surface scanning may also include bands, disks, or patches that are used externally.

If a surgical instrument is guided toward the target tissue, a reference database may be stored as an internal reference within memory 174, or contained within a programmable probe memory and transmitted to memory 174, for use in determining the probes location and/or accuracy of placement. A reference database may contain various information needed to make location decisions, such as key features used to discriminate a contrast agent from other signals, or optionally including a library of characteristic discriminant features from previously identified tissues. Information in this database may then be used by engine 184 in determination of camera or probe location.

Of note, when light from a noninvasive or invasive system penetrates into tissue, the photons traveling between the light source and the light detector take a wide range of paths. The present device takes advantage of this effect as the scattering provides an averaging and volume sampling function. When detected illumination is measured after it has propagated through the tissue over substantially non-parallel multiple courses taken through the tissue between the time the photons are emitted and then detected, many regions of the tissue can be sampled, not merely the tissue on a narrow line between emission and detection. This allows a small but important feature, such as a small tumor, to be detected even if it happens outside of the line directly between the light source and light detector.

EXAMPLES

The breadth of uses of the present invention is best understood by example, ten of which are provided below. These examples are by no means intended to be inclusive of all uses and applications of the apparatus, merely to serve as case studies by which a person, skilled in the art, can better appreciate the methods of utilizing, and the scope of, such a device.

Example 1

Mathematical Simulations

To model the effect of gating an optical camera system, we simulated the optics of tissue and cancer using a computer model developed for this purpose. This model incorporates data regarding measured light levels in an operating room, measured reflectance of light from exposed human tissues, optical contrast and filter characteristics, and both known and measured collection losses.

There is significant background light in an operating room. We measured human skin in an operating room to have a typical reflected irradiance of up to 3 mW/cm$^2$, or about 10$^{14}$ photons/sec/mm$^2$. The standard deviation, or noise, in this background reflected light is related to the square root of the photon count, or about 10$^7$ photons for a one second measurement.

Now consider a 1 mm wide tumor, in the shape of a sphere, which has been marked using the binding of a contrast agent targeted to a particular cell surface receptor. Such a tumor likely contains approximately 100,000 tumor cells. Most tumor cells have surface receptors that are expressed in concentrations of 10$^5$ to 10$^7$ copies per cell. Experience with nuclear medicine (radioactively labeled) agents has demonstrated that 1,000 to 4,000 copies of an antibody plus contrast agent can reasonably be delivered to each cell by intravenous injection. This number is likely higher for agents targeted using small peptides, such as amino acid dimers (with two amino acids) to decamers (with ten amino acids). Using the case of the antibody targeted dye as a worst case, between 1 and 20 fluorescent dye molecules have been placed on each antibody of type IgG or IgM, with a usual range of 2–4 dye molecules per antibody for IgG. Assuming 4 dye molecules per IgG antibody, and 2,500 antibodies delivered per cell, this yields 10,000 dye molecules delivered per cell. For a 1 mm tumor, this translates into a total of 10$^9$ dye molecules in a 1 mm$^3$ sphere, or 3.2 nM dye.

In room light, under additional illumination by a CW (continuous wave) diode laser with an average power of 1 mW, and a dye with a quantum efficiency of 0.28, these molecules would emit 3×10$^8$ photons/second. This compares poorly to room light, which would overwhelm the dye signal by over 5 orders of magnitude. With this disparity in signal and noise, only 50 dye photons would be detected for each 1,000,000 ambient photons collected. Under such conditions, a 12-bit intensified camera would overflow before detecting any dye photons, while a high-quality 16-bit intensified camera would detect only 3 dye photons before overflowing. For both of these cameras, a 1 mm wide target sphere would not be reliably detected. Note that this disparity between ambient and dye photons also prevents background subtraction from being effective in ambient light, in the absence of an improvement in signal to noise.

Two key methods to improve signal to noise are a) substantially rejecting the strong ambient light while preserving a weaker target signal, and b) enhancing the weak or absent target signal in vivo. Improvements using either one of these methods, or in both, would immediately result in a measurement substantially enriched (>10$^4$, or perhaps 10$^6$ to 10$^8$) in signal as compared to the noise, and would be a significant step toward a real-time optical system optimized for human use under operating room conditions.

In view of this, short laser pulse widths and narrow gate times can be used with a gated camera. This allows the detected ambient light to be decreased to 1×10$^8$ photons/sec/mm$^2$ per each 1 μs gate each second, or even decreased down to 1×10$^6$ photons/sec/mm$^2$ per 10 ns gate used each second. If the same total number of illumination photons can be delivered over the gated period as were delivered over 1 second in the example above, then the detected signal will be enhanced in the target photons with respect to the background photons, and the target tissue is well detected, without any increase in the average illumination power. By adding a narrow-band filter to screen out additional room light, the detectable (gated) room light could decrease to as little as $2 \times 10^4$ photons/sec/mm$^2$, well below the intensity of the target fluorescence (however, use of a filter alone in the absence of gating would be insufficient to detect the target signal well).

Now, consider a tumor that is 100 microns across, rather than 1 mm across. A 100 micron tumor has a volume 0.1% of the volume of a 1 mm tumor. In ambient light without gating, the signal from a 100 micron tumor of $3 \times 10^5$ photons/second is well below even the standard deviation of the ambient light counts, and will be lost in the noise. In contrast, this low level of light remains above the ambient light when using a gated detector.

Figure 4B:
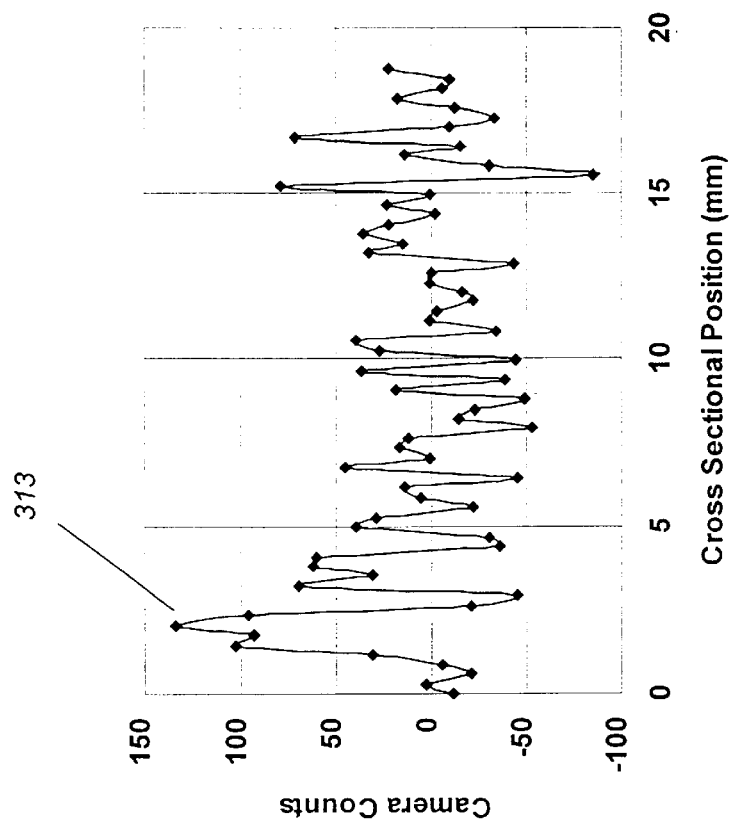
FIGS. 4A–B show a computer-generated image of a 100 micron tumor model, and cross-sectional photon intensity graph through that image, respectively.
Figure 4A:
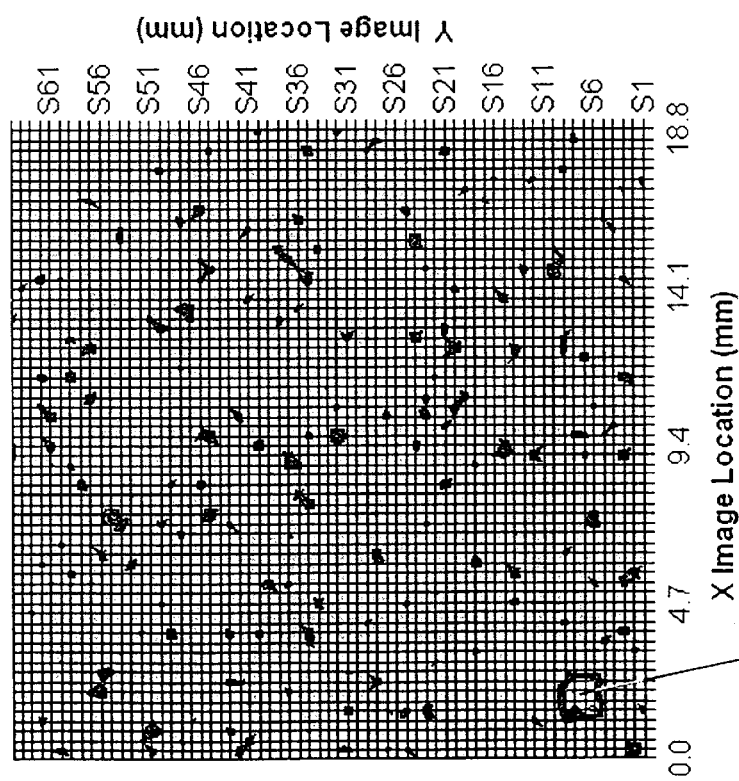

A computer-generated simulation of the optical image of a 100 micron tumor, using the known optical properties of tissue, known levels of ambient light with a peak reflected irradiance of 2 mW/cm$^2$, a 1 mW average illumination power, and expected losses from camera photon capture and lens transmission, is shown (FIG. 4A). In this image, tumor 307, a 100 micron tumor, is clearly visible using a 1 second integration time. A background-corrected graph of the expected photon counts, as determined by a cross-section through tumor 307 in FIG. 4A, is shown in FIG. 4B. After collection losses from the camera and lens (0.03% capture and transmission), the reflected ambient light image has a mean value plus or minus one standard deviation of 521+/−23 counts (n=3,136 pixels), which falls after background subtraction to 1+/−32 counts. In comparison, tumor in ambient light after background subtraction has a value of 136+/−36 counts (n=16 pixels), as shown at tumor light peak 313. These two regions are statistically different (p<0.0001). This model predicts that as few as 100 cells or less may be detectable in real-time using summed 10 ns gating times in ambient light over 1 second.

Example 2

Working Imaging System Validates Computer Model Projections

In order to test the validity of the images generated using the computer model shown in Example 1:, we constructed a working gated camera and laser system as described under the preferred embodiment, and tested this system on a tumor model.

In this experiment, the reflected background light in a dimmed room was adjusted to 0.375 nW/cm$^2$, or 75 million photons/sec/pixel. Although this level of light is well below that which is found in the operating room, a low level of ambient light was required as we wished to test the camera in both gated and ungated modes to validate the improvement achieved through the use of gating. In a more brightly lit room, the ambient light would have overflowed the camera, making it difficult to compare the signal to noise both with and without gating in ambient light.

For a tumor model, we constructed a fiber-based light emitting diode (LED) system that emits a known number of photons, traceable to the National Institute of Standards and Technology (NIST) via an EXFO photometer calibrated at the peak LED wavelength. We adjusted the fiber light source to emit 1 million photons per second from a 200 μm core/240 μm clad buffered NA 0.37 Visible/NIR optical fiber (Polymicro Phoenix, Ariz.), or about the same number of photons expected from a contrast-labeled 125 micron dye-labeled tumor. The CCD chip in the test camera was arranged as 512×512 pixels, and the imaging field of view using an f/0.8 Nikon lens was 15 cm×15 cm. Therefore, each pixel in the image represents a field of view of 300 μm by 300 μm. Under these conditions, the majority of light in an image of the fiber should fall on about 4 image pixels.

The camera was focused to image the tip of the calibrated model tumor light source. For each of four images, a "tumor-off" background sample was taken with ambient light only, then a "tumor-only" image was collected using the LED in the absence of ambient light, and finally a "tumor-on" image was collected in ambient light. To generate the test images, the tumor-off background image was subtracted from the tumor-on ambient light image. These test images replicate the situation in the operating room, in which the illumination source, but not the ambient light, can be turned off and on. In addition, the tumor-only image allowed comparison of the expected number of photons with the detected number of photons, to provide confirmation of our imaging model calculations.

For each image set, the gate time was increased in a stepwise fashion starting at 300 ns and rising to 10 μs, 100 μs, 1 ms, and finally to fully open for 1 second without gating (CW). Each image was collected over exactly one second, using the sum of 100 variable camera gating periods over the course of one second (save for the fully open image, which used 10 ms gating and thus collected over 100×10 ms, or one second on time per second, and this collected all photons received each second). During imaging, the light source was divided into 100 pulses per second, with each pulse lasting 20 ns, such that tumor model emitted a constant total number of photons during the gated-on periods of the camera. In this manner, the number of tumor model photons reaching the detector while the gate was open did not vary from test to test, while the total number of detectable background photons varied widely. Each image required 1 second to collect, while display was nearly instantaneous after collection (<100 ms).

Figure 5A:
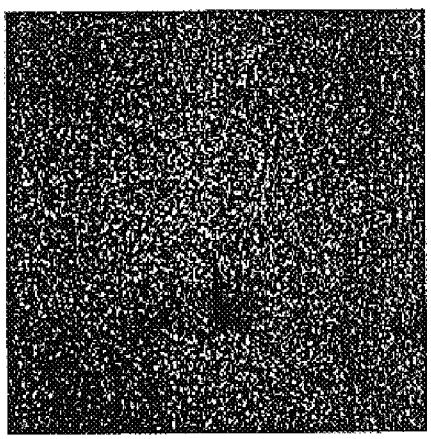
FIGS. 5A–D shows four camera images collected from a point light source in room light with no gating, 100 $\mu s$ gating, 10 $\mu s$ gating, and 300 ns gating, respectively.
Figure 5B:
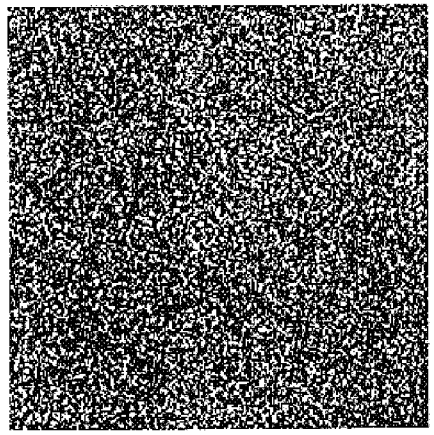
Figure 5C:
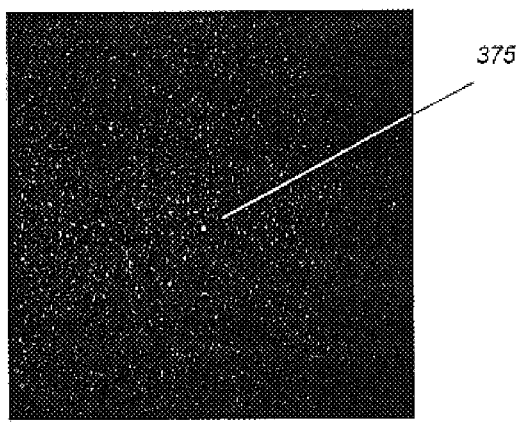
Figure 5D:
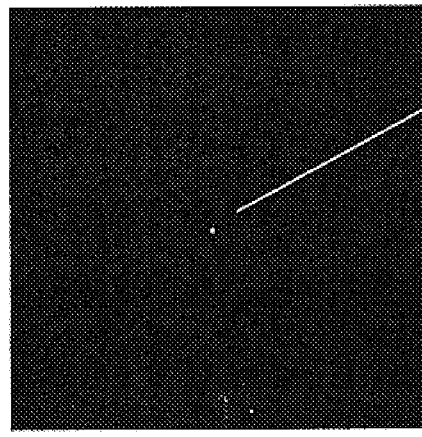

Four images from this experiment are shown in FIGS. 5A–D. With no gating (CW mode, FIG. 5A) and with 100 μs gating (FIG. 5B), the tumor signal cannot be seen, while tumor image 375 is just becoming visible at 10 μs gate time (FIG. 5C), and tumor image 381 is clearly visible and detectable with a 300 ns gate (FIG. 5D).

Figure 6A:
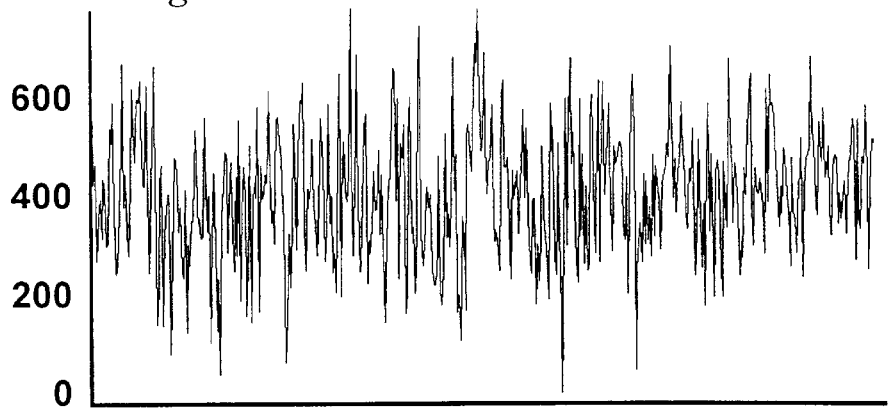
FIGS. 6A–C shows a graph of camera intensities at each pixel for a linear cross section through three of the images shown in FIG. 5, showing intensities with no gating, 100 $\mu s$ gating, and 300 ns gating, respectively.
Figure 6B:
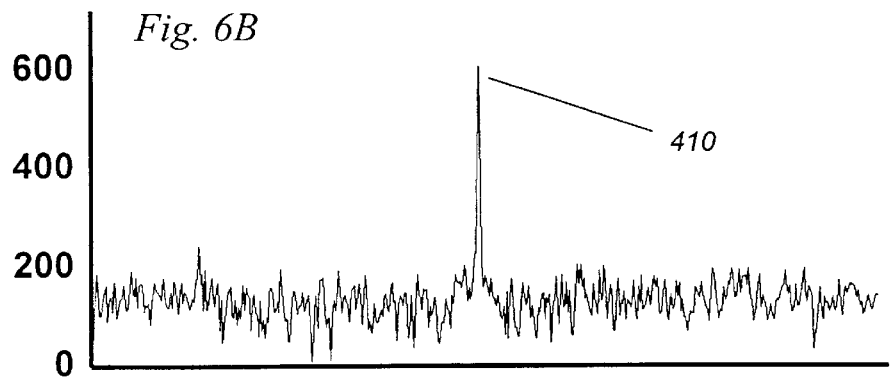
Figure 6C:
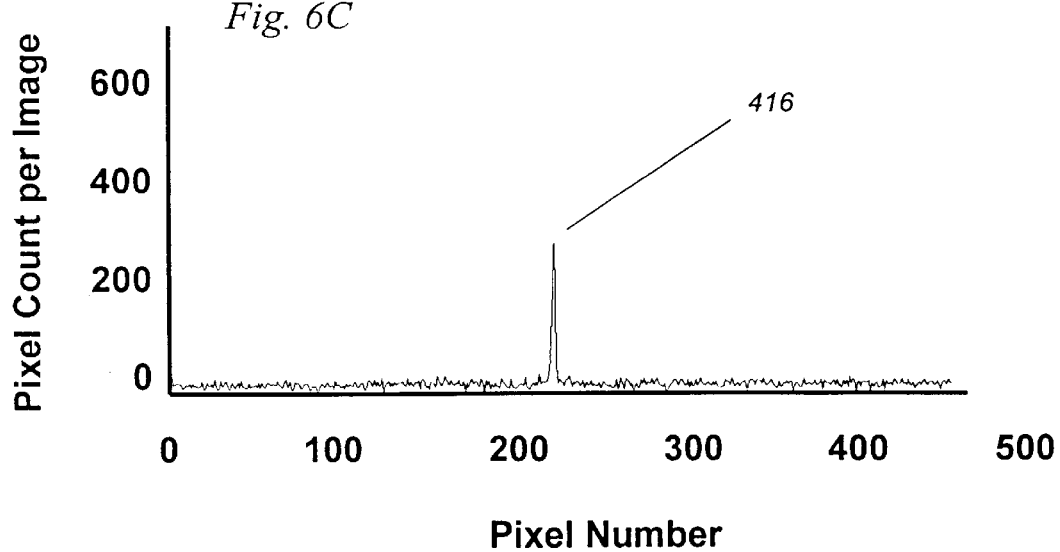

The images shown in FIGS. 5A–D were converted to pixel counts, plotted graphically, and statistically analyzed. Pixel intensities for a linear cross-section through each of three of the images in FIG. 5 are shown in 2-D graphical form in FIGS. 6A–C. The tumor is not visible in the counts displayed for the CW image, while tumor peak 410 is visible in the 10 μs cross-section shown in FIG. 6B, and tumor peak 416 is visible in the 0.3 μm graph as shown in FIG. 6C. The tumor-only images (not shown) were used to measure the strength of the laser signal as measured by the ICCD, in order to ensure that a similar number of photons were detectable at each setting. The following table (Table 1) summarizes the image statistics for the 3-D images shown in FIGS. 5A–5C and the graphical plots FIGS. 6A–6C and for images not shown.

TABLE 1

Camera counts for a tumor model emitting light levels expected for dye-tagged tumors in vivo, imaged in ambient light at different gating times. With no gating (CW mode) and with 1000 µs gating, the tumor signal is not statistically detectable, while it is clearly visible and detectable with the 10 µs and 0.3 µs gates.

| Gate Time (µS) | Duty Cycle (%) | Background Signal (mean ± S.D.) | Target Signal | Signal to Noise Ratio | Enhancement | # of Pixels Brighter Than Tumor |
| --- | --- | --- | --- | --- | --- | --- |
| 0.3 µs | 0.003% | 2 ± 0.12 | 181 | 297:1 | 7,453:1 | 0 |
| 10 µs | 0.1% | 25 ± 13.5 | 491 | 7.2:1 | 1,617:1 | 0 |
| 100 µs | 1% | 374 ± 54 | 509 | 1.9:1 | 112:1 | 0 |
| 1000 µs | 10% | 3,634 ± 165 | 470 | 0.56:1 | 11:1 | 604 |
| C.W. | 100% | 36,810 ± 393 | 447 | 0.22:1 | 1:1 | 3,527 |

In practice, tough the total number of photons collected from the tumor model was intended to be constant, a decrease in signal was seen at shorter gating times, as indicated by the lower target signal counts at the shorter gate times in Table 1. This was found to be due to a 1 µs emission "tail" of the calibrated light source during powering down, which was increasingly clipped and lost as the gating time was shortened, resulting in lowered target signal counts. With respect to the data collected, this tail actually makes the above results more striking, as the error introduced by using a target of lessened intensity would only have made the tumor model less detectable, not more detectable, at short gate times.

Next, the detectability of the tumor model was assessed. In a 512×512 pixel image there are 256,000 pixels. In order to detect a 200 µm tumor filling approximately only one to four pixels, only a few pixels in the entire image can be marked as tumor if the tumor is to be detected. For this to occur, the tumor threshold must be placed at 5.07 S.D. above background. Using a standard camera mode (CW), tumor signal of 447 counts (measured in the dark) becomes lost in the large noise during imaging in ambient light (ambient background of 36,810+/−393 counts). As a result, there are 3,527 pixels in the image with similar or greater intensities to the tumor. The signal to noise for this image is 0.22, where signal to noise is defined as peak tumor signal intensity divided by 5.07 times the S.D. of the background intensity. Similarly, the tumor is not reliably detected using a wide gate (1000 µs at 100 Hz), with a signal to noise of 0.56. In comparison, when the gate width is 0.3 µs at 100 Hz, the source signal (491 counts) is easily seen above the ambient light (25+/−13.5 counts). Here, the signal to noise is 297:1, and there are no other pixels in the image with counts greater than or equal 5.07 S.D. of the background, save for the source signal.

This improvement in detectability with gating is the result of the enhancement of the fraction of target signal to background signal photons in the detected sample. In this example, the enhancement rises from 1-fold (no enhancement) without gating to 7,453-fold with 0.3 µs gating at 100 Hz (Table 1, above).

This information could be presented to the user in a number of ways. For example, those pixels equal to 5.07 S.D. or greater pixels could be marked in bright colors, and overlaid upon the black and white image of the subject. Alternatively, pixels at 2, 3, 4, and 5 S.D. could each be assigned their own artificial color, such as from cold blue to hot red, with increasing significance. Alternatively, the word "Tumor" could be displayed on a monitor. Another alternative is that the p-value of tumor presence could be displayed.

Note that the number of photons captured by the imager is significantly less than the number emitted from the tumor model. This is largely due to lens and distance losses. For example, a 25 mm lens placed 30 cm above a sample collects only about 0.13% of the light emitted in all directions, and still only a small fraction of the light emitted from a forward-directed fiber, regardless of the quality of the lens. Further, lens coatings, reflection losses, photons out of the focal plane, and other lens related problems combine to produce a lens efficiency of about 75% (that is, ¾ of the collected light incident on the front of the lens passes through to the image intensifier on the other side of the lens). Other losses also contribute to the lower than theoretical signal strength. For example, ICCD cameras also have efficiency curves that produce photoelectrons in the intensifier from 10% to 40% of the time a photon hits the intensifier aperture. Also, the gain in the intensifier can vary depending on user settings from under 1 to above 1,000. In the system tested for this example, the ICCD was calibrated using a NIST traceable standard, and was found to produce 1 camera count for every 3 photons incident on the photocathode surface of the image intensifier. Combined with the known 0.26% efficiency of the lens photon capture, the total efficiency of photon capture for the system as described is a mere 0.05%. This agrees with the measured efficiency (actual ICCD counts divided by one million photons per second emitted by the tumor standard) of 0.04–0.05%.

There are methods to decrease the photon loss. For example, the ICCD could by coupled directly to the tissue by a fused fiber array. The filter could be deposited directly on the fiber array, to reduce any blurring of the direct-coupled signal with free space travel. This would increase the photon capture by over two orders of magnitude. Such an improvement would be within the spirit of the present invention.

In this example, the tumor model is well detected with a signal enhancement of less than $10^4$. This low enhancement was successful in this experiment in large part because the ambient light had been lowered to prevent the CCD camera from overflowing during the CW image test. In practice, the surgical field is more brightly lit than in the experiment performed here, with ambient light up to 10,000 times brighter, or more. When the background light level is increased to values expected in the operating room, the standard intensified camera becomes worse at detecting tumors than is shown in the experiment shown in Table 1. The addition of narrow band-pass filters reduces the detected light to be 10–100 times brighter than used in this experiment, while shorter gate times allow for good ambient light rejection and a good signal to noise using a 10 µs gate or less to see a 100 µm tumor, or about 100 cells, using a relatively weak laser.

Example 3

Imaging of a Dye Coupled to Antibody in Ambient Light Ex Vivo

Using the camera system described in Example 2, we added a synchronized laser light source and demonstrated the ability of the system to image trace quantities of an antibody-coupled dye, present in the same concentration and volume as expected in vivo for similarly sized tumors labeled using antibody-targeted dyes.

As noted in Example 1, the concentration of dye in a tumor is about 3.2 nM dye. In this example, we diluted Cy 7 dye (Nycomed Amersham, Buckinghamshire, England) in a free-acid form using serial dilutions to provide the same number of dye molecules per unit volume as expected to be found within an antibody-labeled tumor. Intermediate dilutions of dye were verified using a spectrophotometer measuring at 760 nm, a wavelength for which the extinction coefficient of Cy 7 is about 200,000 per cm per molar solution.

Next, we placed measured volumes of dye, equivalent in size and dye content to tumors of the diameter 12.5 mm (1.00 ml), 4 mm (35 µl), 1.25 mm (1 µl), 0.90 mm (0.40 µl), and 0.25 mm (10 nL). Background light was increased from the level used in the experiment described in Example 2 until it was equivalent to the ambient light in a well-lit operating room, excluding the surgeons headlamps and overhead spot lights. Laser-only dark images were also collected to verify the accuracy of the count estimates. Images were then background subtracted (laser on minus laser off), and integrated at 770 Hz for one second with a gate width of 10 µs.

Figure 7:
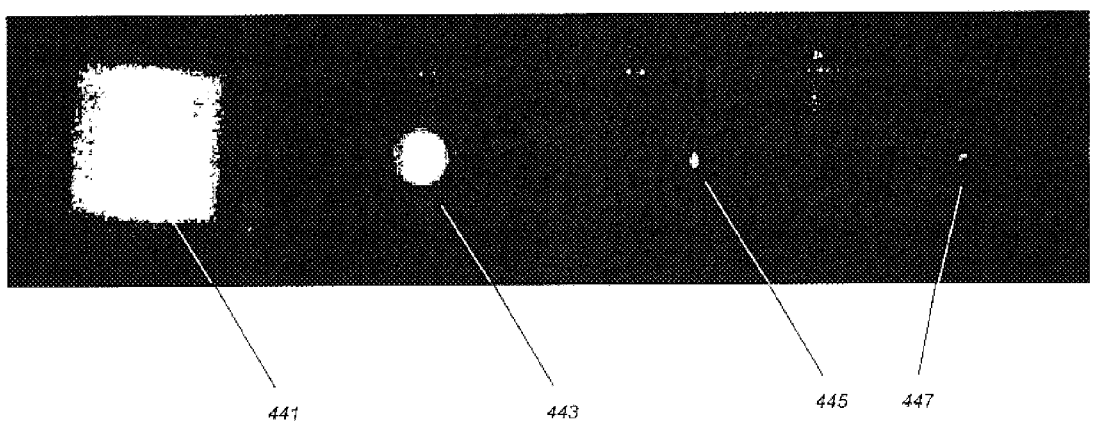
FIG. 7 is a fluorescence image of dye-containing tubes and droplets, equivalent in size and in peak brightness per pixel to the size and peak signal expected for dye-labeled tumors measuring 1 mm, 300 μm, and 100 μm diameter in vivo.

An image of one series of droplets on a slide is shown in FIG. 7, with a 12.5 mm tumor shown at 441, a 4 mm tumor shown at 443, a 1.25 mm tumor shown at 445, and a 0.25 mm tumor shown at 447. Images were also converted to ICCD counts and statistically analyzed. In contrast to the experiment in Example 2, where only 1–4 pixels were illuminated, a variable number of pixels were illuminated in this example, allowing p-values to be calculated for each tumor size. The following table (Table 2) summarizes image statistics from this experiment:

TABLE 2

Camera counts for cubes or spheres of fluorescent dye at concentrations equivalent to that expected in the living animal using antibody-targeted dyes. Extrapolating from this data, tumors down to 0.17 mm will have peak values more than 5.07 S.D. from the mean background using this particular laser diode and dye.

| Equivalent Tumor Size | Tumor Volume | Ambient Signal (mean ± S.D.) | Target Signal (mean ± S.D.) | Total Counts From Target | p-value of mean* | Peak Value | p-value at Peak* |
|---|---|---|---|---|---|---|---|
| 12 mm | 1.0 ml | 288 ± 103 | 8,031 ± 827 | $1.60 \times 10^7$ | p < .0001 | 12,049 | p < .0001 |
| 4.0 mm | 35 µl | 232 ± 96 | 5,227 ± 744 | $1.10 \times 10^6$ | p < .0001 | 7,126 | p < .0001 |
| 1.2 mm | 1.0 µl | 312 ± 83 | 1,203 ± 140 | 31,346 | p < .0001 | 2,726 | p < .0001 |
| 0.90 mm | 0.40 µl | 233 ± 91 | 752 ± 120 | 10,296 | p = N.S. | 2,424 | p < .0001 |
| 0.25 mm | 0.25 µl | 299 ± 138 | 495 ± 341 | 2,864 | p = N.S. | 1,724 | p < .0001 |

A peak values vs. tumor size plot (not shown) indicates a logarithmic relationship between peak value and tumor size listed in Table 2, above. Using this relationship, we conclude that tumors at least down to 0.11 mm have statistically detectable peak values, while tumors down to 0.17 mm will have peak values 5 S.D. from the mean background using this particular laser diode and dye. From this experiment, we conclude that tumors as small as 0.17 would be reliably detectable in this experiment when labeled with a targeted dye. Such tumors contain as few as 500 cells, or less.

There are certain advantages that arise specifically from the use of signal-enhancing optical contrast. One advantage is to give a detectable optical signal to a tissue or cell type that has little inherent optical contrast. This optical signal can be very bright when compared with contrast agents for MRI, CT, or compared to emitters for PET and nuclear medicine. For example, the local contrast from a targeted fluorescence contrast agent may be 1,000,000 times greater than the contrast signal achievable from a similarly targeted radioemitter. This allows greater signal production while using relatively smaller doses of contrast agent, and provides the signal to noise needed to detect trace amounts of labeled tissue, in theory down to 100 cells or less in vivo and in real time.

In this example, the signal detected from the contrast was a fluorescence signal. While fluorescence is ideal for the imaging system as described in the preferred embodiment, optical contrast agents are advantageous in that they can achieve their contrast in a number of ways. The interaction with the illuminating light that provides the contrast can include absorbence, polarization, optical rotation, scattering, fluorescence, Raman effects, phosphorescence, or fluorescence decay, and measures of a contrast effect may reasonably include one or more of these effects. Examples of optical contrast agents includes isosulfan blue or other absorbing contrast agents, indocyanine green, porphyrins, cyanine dyes, or other fluorophores, methyl red (a pH-responsive dye) or other biologically responsive dyes, colored or fluorescent proteins and other gene products, nanocrystals, quantum dots and other spectroscopically distinct physical constructs, and contrast-filled micelles. Methods of detecting the contrast therefore may include measurement of diffuse light, gated time resolved or frequency-resolved methods, hyperspectral detection or imaging, and the like, provided that the system can be arranged to operate in ambient light.

Optical contrast agents may be administered to a subject in a pre-active (pro-drug) form, and the production of contrast is then achieved by a bioactivation step in which the contrast agent requires activation through a biological interaction before producing, reducing, or altering its native signal. Such interactions include enzymatic processing, conformational changes, receptor binding, gene expression, and the like. For example, a conformational change can be the result of a pH change or of a binding event that swings fluorescence quenching groups into or out of position, decreasing or increasing the signal in response to binding. Similarly, an enzymatic processing may be an irreversible cleavage that removes fluorescence quenching moieties from the contrast agent, turning on a strong signal. Last, a bioinactivation step can be used to shut off the contrast in response to a biological event.

Another advantage of optical contrast is that the contrast agent may have contrast function for other imaging modalities, such as MRI, CT, and others. This allows monitoring by more than one modality at a time.

Another advantage is that by careful selection of the contrast agent, optical signals that differ markedly from native optical signals (such as native porphyrins) can be selected for imaging, giving a lower background signal than is present for contrast agents based upon tissue components already present at some level within non-target tissues (such as ALA, and photodynamic therapy precursors, which are metabolized to porphyrins, already present in low amounts in normal tissues).

Example 4

Imaging of an Antibody Coupled Dye in Ambient Light Ex Vivo

Figure 8:
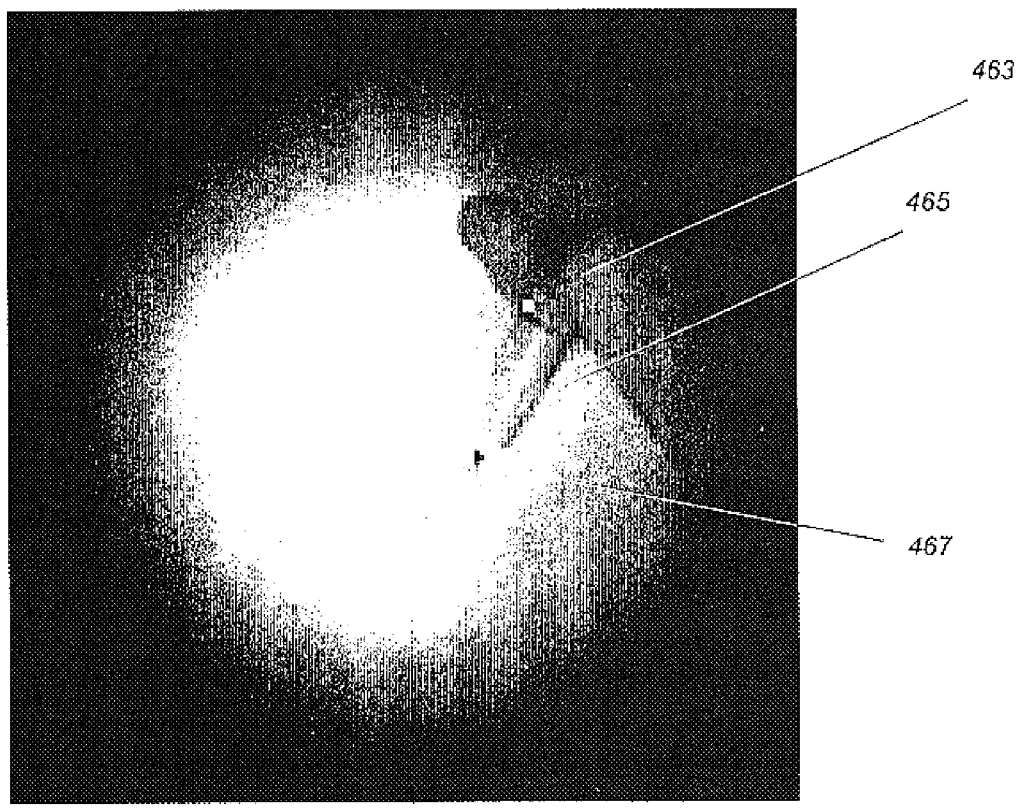
FIG. 8 shows a black and white image of a hand holding a tube of Cy 7 coupled to antibody merged with a color overlay indicating the location and intensity of the dye.

A sample of Cy 7 dye coupled to an antibody was imaged ex vivo (FIG. 8). In this example, hand 463 holds micro test tube 465, which contains 20 µL of 10 mg/ml of antibody-coupled Cy 7 dye 467. Hand 463 and tube 465 were imaged with the laser and ICCD gating-grid off to create a black and white image subject image. Next, the laser was illuminated to collect a fluorescent sample image. Finally, the laser was left off, and a third image of the hand was collected to allow for background correction of sample image. This sample image colorized using a false color scale representative of the intensity of the dye signal. Last, the two images (subject and background corrected sample) were fused to form a black and white image with a color overlay indicating the location of dye, as shown in FIG. 8.

In this example, the coupling of the dye to an antibody did not interfere with the ability of the dye to generate a fluorescent signal. In fact, in this case, by shifting the emission farther away from the illumination wavelength, the antibody increased the detectability of the dye.

A strength of using optical contrast is that the contrast agent itself can be quite small, allowing delivery to and targeting of specific tissue sites, including nearly any tissue or cell region. In this example, the dye was coupled to a targeting antibody. Once a system, dye, and method have been demonstrated effective in humans, then the target tissue of the dye-antibody conjugate can be altered merely by cassetting in (substituting) a new antibody, providing great flexibility in applications development.

A wide variety of contrast targeting methods exist, In this example, the targeting moiety was an antibody, but a contrast agent may achieve its localization by chemical or physical means, and such targeting methods are well known to those skilled in the art. For example, the contrast may distribute on the basis of solubility, diffusibility, transport protein affinity, or the contrast may be bound, ionically or covalently, to a localizing moiety such as an antibody, antibody fragment, receptor or translocator binding site or substance. Alternatively, the contrast agent may be bound or encapsulated, such as in a microbubble or liposomal structure, and the surrounding structure may then be targeted using surface structures. Examples of target sites include prostate cancer targeted by PMSA antibodies, breast cancer targeted by Her-2/neu antibodies, lung cancer targeted by somatostatin-receptor octopeptide analogues, and the like. Targeted receptor binding sequences for certain cancers are known to exist in the body for certain cancers, and for other diseases as well.

Example 5

Imaging of an Antibody-Coupled Dye in Ambient Light in Vivo

As noted earlier, even the best conventional imaging methods frequently miss tumors smaller than 1 cm in diameter, while a good pathologist misses a 1–2 mm tumor in an excised surgical specimen about 30% of the time (a 1 mm tumor contains about 100,000 tumor cells, more than enough to lead to recurrence of the cancer).

In order to test the ability of the present invention to help a surgeon locate and quantify tumor in the body, we demonstrated imaging of dye coupled to antibody in vivo.

First, we injected dye into a mouse. The antibody-dye conjugate was rapidly absorbed by the mouse liver, and excreted into the small intestine, allowing the transabdominal image of a mouse shown in FIG. 9 to be obtained. This image demonstrates the allowance for a localization of the contrast agent in vivo. In this image, mouse 520 is shown in black and white, while the detected antibody-coupled dye 531 is shown in color. This demonstrates that if targeted dye, in this case antibody-coupled dye, can be delivered and functionally localized to a region within a living body, in this case the abdomen, and that such dyes can be detected and imaged in living animals. Proof that the signal is transabdominal is shown in FIG. 9B, in which the skin of the abdomen of the same animal shown in FIG. 9A has been opened and moved to the side, exposing the abdominal viscera. There is signal at injection site 543, as well as signal from small intestine 546, arising just distal to the hepatic drainage.

Figure 10:
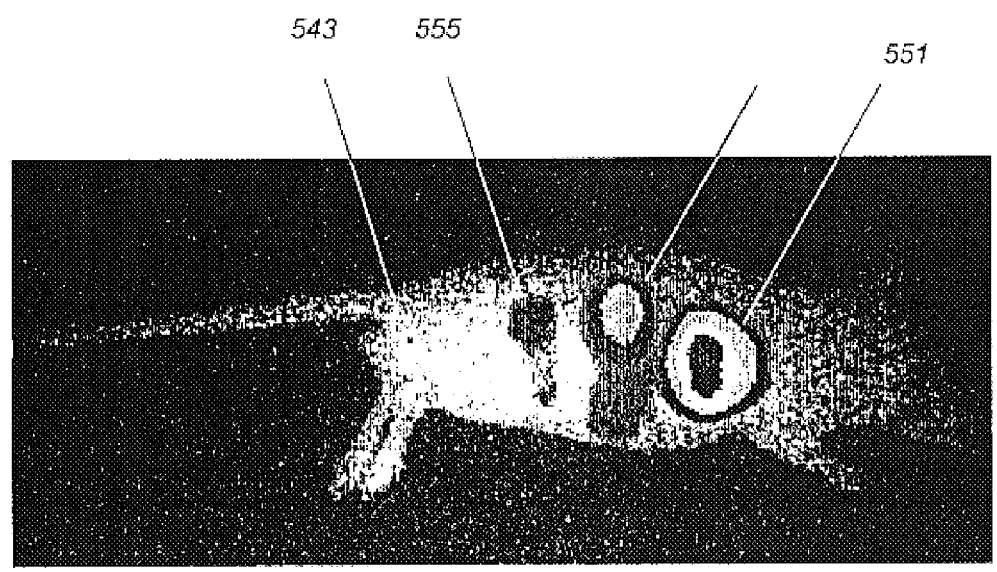
FIG. 10 shows a noninvasive overlay image of a mouse with a graded series of dye injections into the skin of the mouse.

Next, we imaged a series of graded intradermal injections, using three different concentrations of dye, thus demonstrating the ability to quantify dye the signal in vivo, as shown in FIG. 10. For demonstration of a quantitative approach, the three injections should show peak counts in a ratio related to the amount injected, in this case having expected ratio of 1:10:30. In FIG. 10, mouse 543 has injections of 0.10 cc of dye at 4.1 µM at 551, 0.41 µM at 553, and 0.13 µM at 555. The data from that series was digitized, and plotted for total optical signal versus dye injection amount. These data show that the dye load can be quantitatively monitored, raising the possibility that the present invention can not only detect and image a target tissue, but quantitate the tissue or tumor volume as well. Peak counts from this experiment are presented in Table 3, below:

TABLE 3

Photon counts from different concentrations of dye as compared with actual dye concentration. There is a linear increase in photon count as dye molecule count rises.

| Spot No. | Conc. | CCD Pixel Counts | Count Rate (counts/$\mu$s) | Expected Count Ratio | Actual Count Ratio |
|---|---|---|---|---|---|
| 551 | 4.10 $\mu$M | 42,131 in 0.5 $\mu$s | 84,262 | 32 | 71 |
| 553 | 0.41 $\mu$M | 21,653 in 5.0 $\mu$s | 4,331 | 3.2 | 4 |
| 555 | 0.13 $\mu$M | 11,849 in 10 $\mu$s | 1,185 | 1 | 1 |

In this example, the targeted agent was injected locally. However, one advantage of optical contrast is that administration of an optical contrast agent can be performed in a number of ways. Contrast agents can be injected, ingested, or even synthesized within the subject using genetic mechanisms or encapsulated biofactories. In the genetic example, contrast can be delivered as a gene, and the gene product synthesized within the subject is a protein or product that interacts with illuminating light field. Further, as methods are known for the delivery of the contents of a viral particle into a living mammalian cell, contrast agents, or the genes encoding for a contrast agent, can be delivered to a subject by means of a virus that "infects" tissues with a contrast agent. This virally delivered contrast agent can be a pro-drug that requires activation, and is activated when placed into a cell containing certain proteins or ribonucleic acid sequences. This allows for the production of contrast in cells expressing certain internal genetic traits, even if no identifying cell surface receptors exist on the target tissue. Even proteins used in the luciferase emitter reporter system can be made to reactively emit light as a contrast agent when illuminated.

As a second example, contrast can be sprayed or delivered from the tip of the invasive instrument, and used to bathe or infuse the tissue nearby the instrument tip, for example using the needle shown in FIG. 3C The signal from this contrast can then be monitored locally to define tissue margins or detect the presence of certain tissue types, such as tumors. Such an approach can be particularly powerful as a way to guide a tool to remove tissue, and the tissue can be considered removed when local infusion of the contrast agent no longer produces a tissue optical signal. As a last example, optical contrast can be encapsulated in liposomes, allowing a high number of dye molecules to be delivered to a single site.

Once delivered, the contrast may need time to achieve localization in the tissue. For example, a blood-borne contrast agent, if not optically inactive when injected, will need time to accumulate in the target tissue, as well as time to diffuse out of the bloodstream. If the dye is activated at the target site, then loss of the dye from other tissue sites will not be as relevant, as unactivated dye will not produce a background signal.

Another important use of such targeted dye systems may be in animal research. Use of dyes could substantially reduce the time required to perform animals studies, as well as reduce the number of animals required to perform each study. For example, once a cancer promising cancer treatment is identified in the laboratory, it is tested in animals (typically in mice). In order to study the new drug, a large group of animals are given an implant of cancer. At each time point in the treatment, a group of animals are sacrificed in order to allow pathological study of multiple organs and sites. As each mouse will have a slightly different cancer at the time of implantation, many animals are needed for study at each time point, with some subset of these mice killed and studied at each time point. Further, the study of some cancers may require many weeks or months of study until the growing cells, and their distribution, can be fully understood.

As an example of use in animal research, if 5 mice under treatment for their cancer are killed at each time point, and time points occur every two weeks for 6 months, this totals to 60 mice needed to assess the treatment, plus an identical number to serve as controls, for at total of 120 mice over six months. Of note, pathology generally requires 10,000 to 100,000 tumor cells in order to detect a cancer using standard pathology. In contrast, if an antibody can be made against the cancer, and the distribution of a dye-coupled antibody is imaged, then each mouse will receive a contrast inject 3–5 days prior to imaging (shorter if a peptide targeted agent is used). At each time point, each of the 5 animals for drug test and each of the 5 control animals can be imaged. However, since the animals are not killed, all 10 mice can be used at the next time point, and so on. Further, since there is less variability in the disease model when the same mouse is used from time point to time point, the test statistics are improved. Last, since the targeted dye can detect cancer at a very early stage, well before it is seen on pathology, the studies will likely be shorter in duration, with a better statistical result. Thus, in this example, a targeted optical dye approach would reduce animal use from 120 to 10, improve the quality of the data, and shorten the study period from 6 months to perhaps as short as 4 to 6 weeks.

This data also has relevance to guiding surgery, diagnostic, and therapeutic procedures, as discussed in the following three examples.

Example 6

Guiding an Invasive Surgery for Clean Margins

This inability to detect target tissues such as cancer in real time has a profound impact on cancer diagnosis and treatment. The mainstay of treatment for most solid cancers remains surgical excision and removal. Because of the inability to identify cancer, surgeons tend to err on the conservative side during surgery and take wide margins of normal tissue whenever possible, in order to increase the odds of complete tumor resection. Despite this, it is common to miss small islands of cancer during surgery, leading to residual cancer cells outside of the surgical excision. These residual cells, called positive surgical margins, occur in 10–40% of many cancer surgeries. Patients with residual disease have a much higher incidence of recurrence, and die more frequently than other patients. Accurately knowing the margins of disease in a diseased organ would allow for the disease to be completely removed while sparing the maximum amount of normal tissue.

The experiment shown using the subcutaneous injection of dye (Example 5, above) demonstrated how bright the optical signal can be in vivo when the dye is localized near the surface. Tumors are often similarly close to the surface when a surgeon is excising a tumor. In this case, the surgeon's goal is to produce clear margins in the resection of a tumor. Images that update every few seconds or less would allow the surgeon to use the information as feedback to influences the progress of surgery as it occurs.

Figures 11A, 11B, 11C:
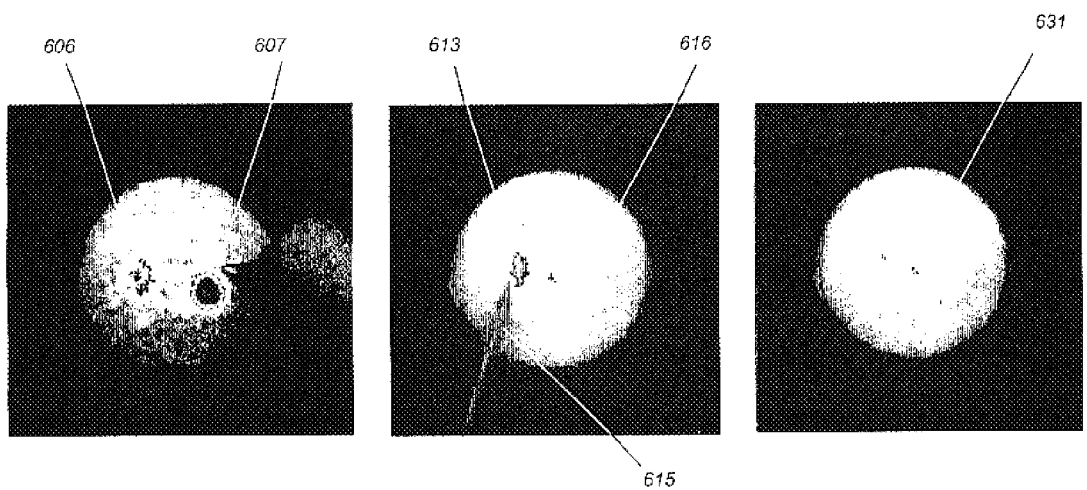
FIGS. 11A–C shows overlay images of a tissue labeled with antibody-bound dye, before, during and after contrast-guided surgical removal of the majority of dye-containing tissue.

We demonstrated that signal from a dye can be used to obtain clean margins. In this example, we injected 100 µl of dye coupled to antibody into 0.4 g of a homogenized bovine liver paste. In the real-time image, the number and location of the two dye regions, region 606 and region 607, are well visualized, as shown in FIG. 11A. The tissue shown in was then cut by a blinded observer who had instructions to remove the labeled tissue, but without knowing the lesion number or location. The observer relied upon feedback and guidance from the imaging camera display, updated twice a second, until all dye was removed. A view of the tissue during the excision of lesion 613 is shown in FIG. 11B, with instrument 615 visible in the live image. Note that labeled tissue 607 has been completed removed, leaving indentation 616. After surgical removal of the dyed tissue, only a trace of dye-containing tissue remains, no dye could be detected at site 631 as shown in FIG. 11C.

The surgical site was then enlarged and tested for residual dye in the remaining tissue. In this experiment, residual dye in the muscle was undetectable by spectroscopy, confirming that effective treatment guidance and feedback was obtained.

This type of guidance has direct application to the surgical removal of the prostate, lymph nodes with metastatic cancer, and in breast tumor resection. In each of these cases, a decrease in the number of positive margins would likely result in a decrease in local recurrence with an improvement in 5 year and long-term survival.

Many methods of targeting a contrast agent to cancer can be utilized. For example, it is known that certain cell types possess surface markers, such that cancer cells may have surface receptors that their neighbor cells do not. This allows for contrast agents to be targeted to specific sites, such as by using the Her-2/neu receptor in breast cancer, or the PSMA or PCSA antigen for prostate. Nonspecific targeting through use of photosensitizing agents (e.g., ALA that preferentially accumulate within cancerous tissues through conversion to fluorescent porphyrin intermediates) are less useful, as the signal from these agents can be found in many tissues, making the detection of rare cells difficult against a background noise for the widely-distributed contrast agent.

Once the dye is targeted to the tissue and allowed sufficient time to localize in the tissues, the detection, localization, or imaging of the target signal can be used to provide feedback during an invasive procedure. For example, a surgical tool can be used to nibble at a tumor, and the process can be continued until no further contrast signal remains, signifying that the tumor has been effectively removed and the surgical margins are clean. In this case, the imaging system is not a surgical instrument but a monitoring and imaging system. Similarly, the optical imaging system can be coupled to a surgical instrument via an interlock, such that the tool nibbles only until a particular area is clean of contrast, but then allows other areas to be nibbled, resulting in that only the tumor is removed from the tumor site. Last, this feedback may be used to control any process of cell destruction, such as an ablation process, using the contrast feedback from the targeted tissue. This also allows coupling of the present invention with other approaches, such as conventional image-guided surgery, while allowing for small course corrections in the surgery as a consequence of tissue-guided feedback. This may reduce the errors that arise when a previously collected image is used for image-guided surgery, without reflecting changes in the tissue that have occurred over time, such as changes in position, or that occur as a result of use or placement of the invasive instrument.

The term tissue-guided intervention is used here in contrast to image-guided surgery. In image-guided surgery, the location of a medical instrument is determined in space with respect to a standard medical image, such as a CT scan or MRI scan. In this way, the surgeon can guide the surgery using the CT or MRI image as a road map. In comparison, during tissue-guided intervention, the tissue itself provides the signal, and surgery or treatment is guided by the real-time analysis of tissue. In the present invention, a tissue guidance signal may be provided by the imaging of target cells labeled by a targeted contrast agent, thus allowing the procedure to be tailored to the patient. In addition, tissue guidance and conventional image guidance can be provided simultaneously in the same patient.

Example 7

Guiding Biopsy

A biopsy is frequently performed in the diagnosis of cancer. Areas in which optically guided biopsy would be of benefit are breast cancer and prostate cancer.

In prostate cancer, for example, one in five men will develop the disease, which exceeds even the incidence of breast cancer in women. The standard method of diagnosis is prostate biopsy. When taking a prostate biopsy, a needle is inserted randomly into tissue in a blind attempt to find the cancer, and this has a 20% chance of missing a cancer that is present. Thus, repeat biopsy tests are frequently required. As prostate cancer is not well seen by current imaging methods (e.g., CT scan, MRI, or ultrasound), prostate biopsies are in effect performed blindly. The ability to detect the presence or absence of trace amounts of prostate cancer to guide biopsy would decrease the number of unnecessary and blind biopsies, as well as lower the false negative rate. Similarly, after surgery, when patients receive follow-up care, identifying if and where cancer growth has occurred is difficult. The ability to identify trace amounts of residual tissue, or tumor regrowth, would assist in the management of the disease.

Thus noninvasive detection and localization of target tissue may allow for diagnosis and treatment guidance. For example, localization of a tissue site at which biopsy should be collected may be assisted using a contrast that collects at the target site. Such a device would also be useful for prostate biopsy by indicating in what region the biopsy should be collected. Such a device would also be useful for prostate surgery follow-up. Prostate surgery patients are followed for cancer recurrence. Here, an optical scan could be combined with the ultrasound scanner already in use to image the prostate to show both tissue structure (ultrasound) and whether a tissue is cancerous (optical overlay). Similarly, when breast cancer patients receive follow-up care, an optical scan could be performed to detect local recurrence at the surgical site in the breast or lymph nodes site.

An entire organ, such as the prostate, could be scanned using an external detection probe. For example, if the current imaging system may be reconfigured as a fiber-array coupled rectal probe that is placed in the rectum and near the prostate, after administration and localization of a contrast agent. If the spectrum of the contrast agent is seen or detected during transillumination of the prostate, then the cancer may be detected, whereas if no spectrum is seen then cancer is absent. Such a detection study may then be followed by a contrast-guided biopsy needle for diagnosis, a contrast guided nibbling tool for cancer removal, or using a contrast-sensitive imaging system to image the distribution and tumor load of tumor within the prostate.

Other forms of a detection probe can be envisioned. For example, instead of using an imaging camera, the light emitters and detectors could be placed on the biopsy tool itself, allowing for the targeted delivery of an instrument to the stained region. Further, if the invasive instrument is an interventional tool, a target intervention, such as ablation therapy, could have been performed and optically monitored at the target site.

The information from this detection and localization can be presented in a number of ways, including the display of a word indicating the presence or absence of a specific tissue type, a table (such as the percentage of signal arising for one or more contrast agents), an identification of the contrast-stained tissue by depth, a graph (such as the presence or absence of a tissue type over time, as shown above, or a distance to a target site), a number (such as the distance to an object), an image (such as the location of the target tissue), a localization (such as a measurement of angle and distance of the target tissue), or a displayed word that changes according to the location and concentration of the contrast agent. Different processed images could be displayed, and no undue limitation is intended by the selection of the images shown in the examples provided herein.

The contrast agent used in this example could have been a contrast agent that activates, or "turns on," upon binding or internalization into prostate cancer would give an even greater enhanced contrast. Any optical contrast agent or reporter could be used here, provided that the optical light source and light detector are configured to detect the signal. Configuration of the source and detector include the ability to detect fluorescence, time- or frequency-resolved data, and the like. Such measures can be used for guidance, which can be as simple as indicating where a surgical scalpel should be moved so as to contact a target tissue.

Other types of output may be considered, but fall within the scope of this invention if the signal is a contrast-based guidance signal that represents a function of information related to the presence, location, or distribution of tissues, or is used to guide a probe or device into a position in the body based upon a signal from a native signal, or from an endogenous, targeted contrast, collected in such a manner so as to reduce the ratio of detected ambient light to target signal.

The analysis in this example uses the signal at a single wavelength band, passing through a filter, in order to extract a measure of localization or distribution of the contrast agent or target tissue. Thus, the contrast guidance algorithm can be deceptively simple. For example, if the contrast signal is more than 5 S.D. above the background, then the tissue is marked as the target tissue in an image. However, other algorithms may be considered. For example, when light travels through tissue, the shorter (bluer) wavelengths tend to be preferentially scattered and absorbed, in part due to higher scattering for light of shorter wavelengths in tissue, while the longer (redder) wavelengths tend to pass more easily. By measuring at two wavelengths (either by measuring two regions from the emission spectrum of one dye, or by measuring the peak regions from two different dyes that bind similarly to the target tissue), a depth signal could be generated. With this type of two-wavelength system, the ratio of light at the longer wavelength ($\lambda_L$) to that at the shorter wavelength ($\lambda_S$) would be related to the mean depth of the target tissue.

Various forms of probes may be considered, including needles, trocars, catheters, radio-frequency antennae, cryo-surgery probes, laser surgery beams, endoscopes, video cameras and fibers, and the like. A time-gated hand held probe may be used to locate positive lymph nodes by moving back and forth across the skin, and sounding an alarm when the correct optical pattern is detected. Invasive probes could also be constructed using biopsy needles or catheters.

Last, other tissues other than cancer may be imaged. For example, antibodies to white blood cells could be used to yield an imaging method for inflammatory diseases, while antibodies against the exposed surfaces of unstable plaques in coronary arteries may be used to image sites at which future vascular disease is likely.

Example 8

Guiding Breast Lymph Dissection

In contrast to guiding surgery to clean margins as shown in Example 6, or guiding a needle toward disease as shown in Example 7, a surgical decision may be whether or not to operate at all. For example, the treatment of breast cancer requires determination of the grade and spread of the tumor, a process called staging. Determination of spread to the lymph nodes is a key to proper treatment selection and increased survival. The staging of the lymph nodes is the longest part of many breast cancer surgeries, and is the part that generates the most post-operative pain and complications of the procedure. However, after this invasive surgery, 68% of women are found to have no cancer in their removed lymph nodes, and therefore (in retrospect) underwent a major surgical procedure unnecessarily. The ability to detect, prior to surgery, the presence and location of lymph nodes most likely affected by cancer would allow for a ⅔ of women to skip the surgical biopsy, while allowing for much smaller, targeted surgical incisions, and a less extensive surgical exploration, for those women who do have cancer in the lymph nodes on optical scan.

Lymph node staging surgery involves the removal of the axillary (armpit) lymph nodes. In some cases, only the sentinel lymph node is identified and biopsied. Sentinel nodes are the main lymph node draining the tumor. They area currently identified by injection of a radioactive substance, which is traced using a Geiger counter (e.g., U.S. Pat. No. 5,846,513 discussed under Background), or by injection of a blue dye (isosulfan blue, Lymphazurin™, US Surgical Corporation, Norwalk Conn.) near the tumor, which then migrates to the sentinel lymph node or nodes, staining them blue. Lymphazurin is a sterile, aqueous solution U.S. FDA approved for subcutaneous administration for use in delineating lymphatic vessels, including tracking lymph nodes involved in cancer. This blue dye is easy to spot once the node has been found, but is difficult to find without making an incision.

We suggest that the lymph can be externally localized using targeted lymph contrast. We have already demonstrated that, as the amount of contrast in a sample tissue is increased, the in vivo optical signal linearly increases. We have also previously demonstrated that optical signals penetrate deeply through tissue, and that optical contrast can be used to produce a signal that varies with localization and distribution.

Now, in experimental tests, we demonstrate that isosulfan blue containing regions of tissue can be externally localized and targeted using optical means. In the laboratory, we first demonstrated that isosulfan blue contrast could be detected in mixtures of hemoglobin and contrast agent. As the primary absorber in the body between 550 and 900 nm is hemoglobin, we measured mixtures of hemoglobin and Isosulfan, and found unique features that allow differentiation of isosulfan blue from hemoglobin. Using these unique features, the signature of isosulfan blue could be extracted from hemoglobin mixtures using the slope or value of the first differential signal near 697 nm.

Figures 12A, 12B:
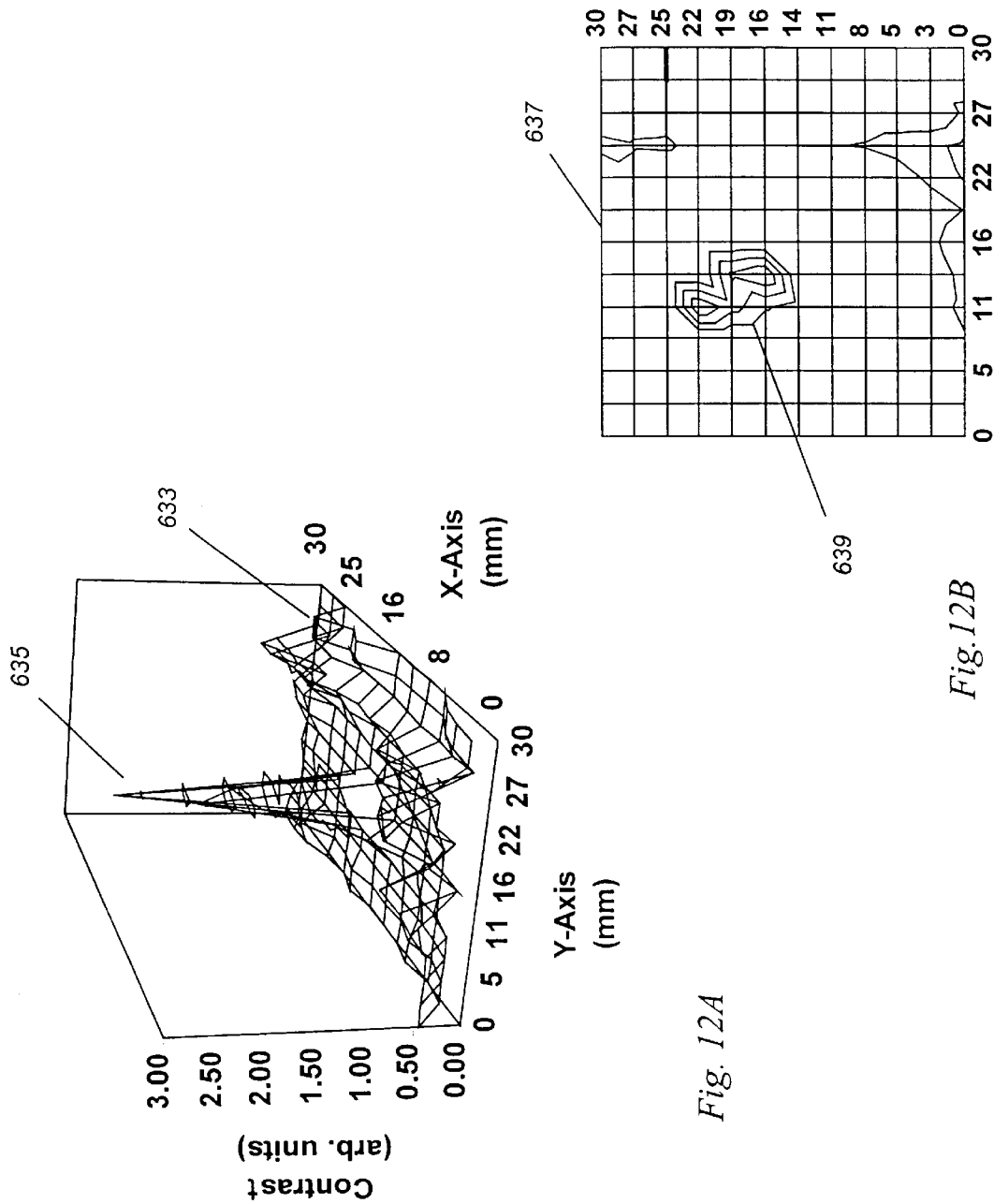
FIGS. 12A–12B show images of a buried optical label.

Next, we used this first differential signal approach to generate an external image of the contrast-positive lymph nodes in a tissue model. The scanning detector for this study used multiple fibers for emission and detection, and serves as a model for an instrument that can be scanned within a wound or on the skin. An isosulfan blue target was created by placing isosulfan on filter paper. A piece of filter paper measuring 2 mm×3 mm, and contained 0.20 $\mu$L of contrast (4 nanomoles of isosulfan blue) was placed 2 cm below the scanning surface in vivo. Data were collected by scanning the detection fibers across the area to be monitored. A 30×30 mm area was scanned, and 10 spectra were collected for each scan pixel. In this case, the fiber was singular, though a 1-D linear array, or a 2-D array, would have worked equally well or better. Data from the above experiment were collected in 2-D by scanning the surface probe over the tissue to collect a grid of data. Image 633 in FIG. 12A clearly shows the location of the isosulfan blue target as contrast signal peak 635. An overhead view of FIG. 12A is shown in FIG. 12B, where it can be seen in image 637 that well-circumscribed area 639 indicates the location and distribution of the isosulfan blue, as well as of the target tissue. Therefore mapping of the positive sentinel nodes in tissue is achievable.

This experiment demonstrates that optical contrast can be used to produce a signal of a buried object that varies with localization and distribution. Such a signal can be used to guide surgery, such as targeting a probe that detects signal increases as the sensor is moved closer to the contrast source. This experiment also confirms that such a system and method can work to form images in vivo via a medical instrument, used externally or internally, to measure light that has traveled through opaque tissues. In this example, the scanned fibers can be replaced with a camera or probe containing a CCD detector, as discussed earlier in Examples 1 through 5. Surface mounted LEDs could replace the illumination source and fibers, to allow rapid and simultaneous imaging of multiple pixels. Such a system would allow reconstruction of contrast maps, as well as guidance toward contrast positive nodes in humans using an optically-enabled invasive instrument.

Last, a fluorescent contrast could be substituted for the dye, and the fluorescence imaged in a similar manner. For example, as isosulfan blue is preferentially passed through the lymphatic system, a fluorescent dye covalently coupled to isosulfan blue could serve as a source of differential contrast in vivo; namely that tissues which take up the contrast agent will appear distinct in their fluorescence from those tissues that do not take up the contrast in similar amounts. Such differential contrast can also be achieved by having the contrast agent bioactivated at the target site, and "turn on" or "turn off" only in desired tissues.

Example 9

Multicolor Contrast Labeling

An inherent advantage to use of optical contrast is that multiple contrast agents, each of distinguishable optical signature in vivo, can be added to provide the power of simultaneous, multiple labeling for different affinities and receptors. Dual or multiple contrast labeling is a technique frequently used in cytology and other ex vivo laboratory disciplines. In this technique, different contrast agents are added to the same sample, in order to extract additional information.

Such dual labeling may have relevance to detection and imaging in vivo. For example, many different tissues may take up a first contrast agent, as each of these tissues has a receptor for the first contrast agent. In addition, a different combination of tissues may take up a second contrast agent, as these different tissues also each have a receptor for the second marker. A cancer may be identified as having both receptors, or the presence of one without the presence of the second, or by the presence of either marker. In such cases, the ability to detect, localize, image, and target using two or more contrast agents simultaneously is likely to have relevance in human studies. In order to image a cell type that expresses two or more different receptors, more than one contrast agent may be required.

Here, we discuss data that confirm the view that dual labeling approach can be applied in vivo beginning with two optical dyes of differing optical characteristics, and detecting both dyes using a fiber based needle. For this experiment, we utilized two different dyes with different absorbence curves, a red contrast (FD&C Reds 40 and 3, Schilling, Hunt Valley, Md.) or Lymphazurin™, a blue dye described in Example 8.

A tissue model was created using thickened, homogenized beef. Volumes of contrast (3 $\mu$L isosulfan blue and 14 $\mu$L red contrast per cc tissue homogenate) were mixed into selected regions of this model into this model, creating regions with different optical characteristics. A layered structure was created, with some regions containing no dye, some regions containing red dye or blue dye only, some regions containing both red and blue dye, and some regions containing both dyes.

An invasive needle with embedded optical fibers was inserted into the tissue. As the needle passed through different tissue layers, multiple spectral features were recorded. This can be achieved, for example, by illuminating with different light source, or by using different filters on the detector. The data were then processed to calculate the strength of the optical signal from each dye.

Figure 13:
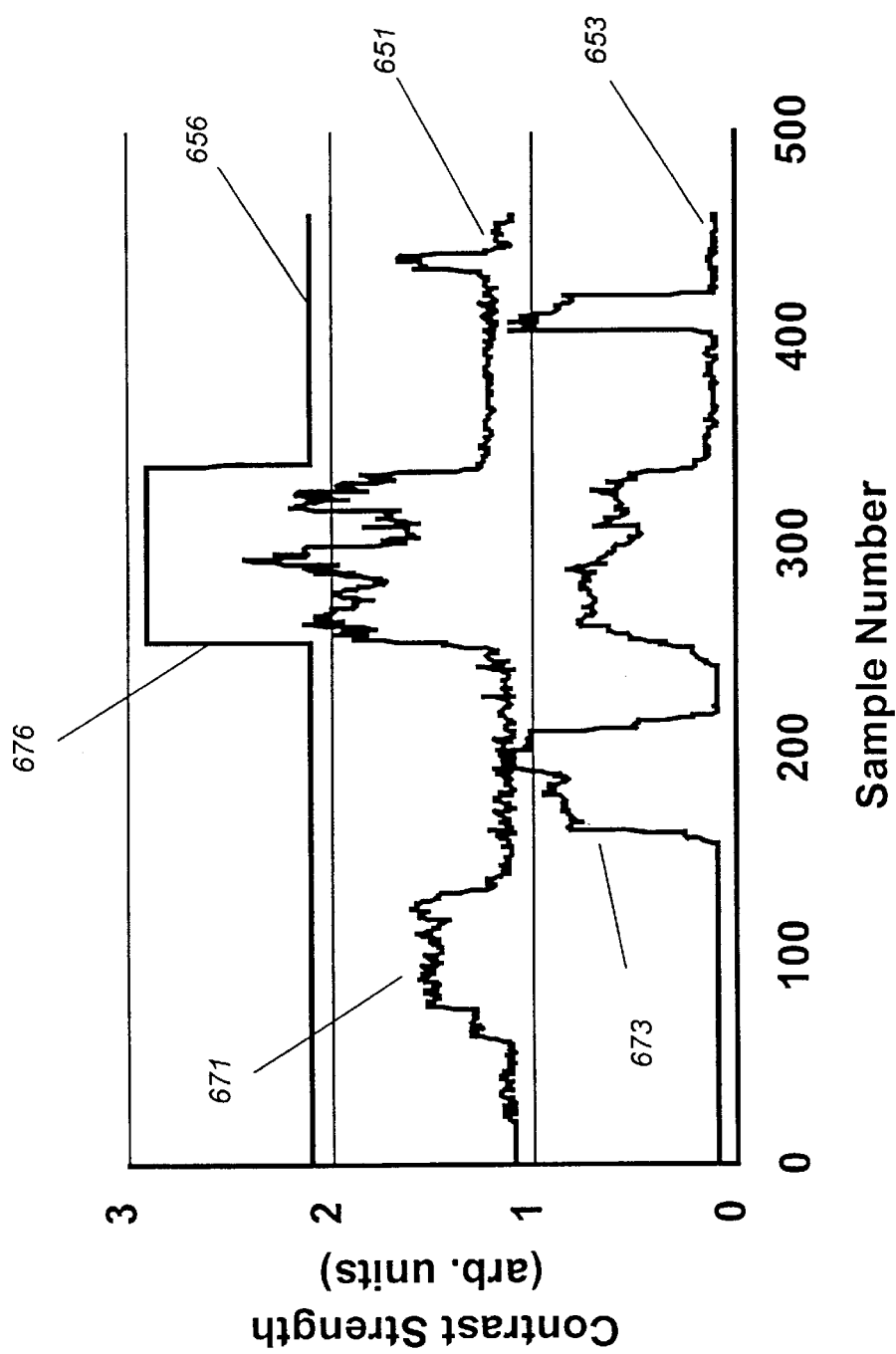
FIG. 13 shows a double label study in which two contrast agents were tracked in a tissue model.

The calculated contrast signal strength for each contrast agent is plotted in FIG. 13. Red contrast strength curve 651, shown offset on the y-axis by 1 unit, was calculated using a differential absorbence feature at 556 nm, while blue contrast strength curve 653 was calculated using a differential absorbence feature near 700 nm. Coincidence curve 656 indicates when both contrast agents are present using a threshold value. A region containing red dye can be seen as peak 671 for sample numbers 62 to 133, a region containing blue contrast alone can be seen as peak 673 for sample numbers 159 through 218, while a region containing both red and blue contrast can be seen from coincidence peak 676 for sample numbers 251 through 335. The region with both the first and second contrast agent is clearly detectable. Three or more contrast agents can be analyzed using similar methods.

This data can be presented in as a graph, as shown in FIG. 13, or the raw data can be listed in table form, as shown below:

TABLE 4

A numeric table of some of the data shown graphically in FIG. 13.

| Sample No. | 0 | ... | 96 | ... | 168 | ... | 268 | ... | 348 |
|---|---|---|---|---|---|---|---|---|---|
| Contrast A: | 0.0 | ... | 1.2 | ... | 0.1 | ... | 0.8 | ... | 0.3 |
| Contrast B: | 0.0 | ... | 0.0 | ... | 1.3 | ... | 1.1 | ... | 0.1 |
| Both A and B: | No | ... | No | ... | No | ... | Yes | ... | No |

Figure 14:
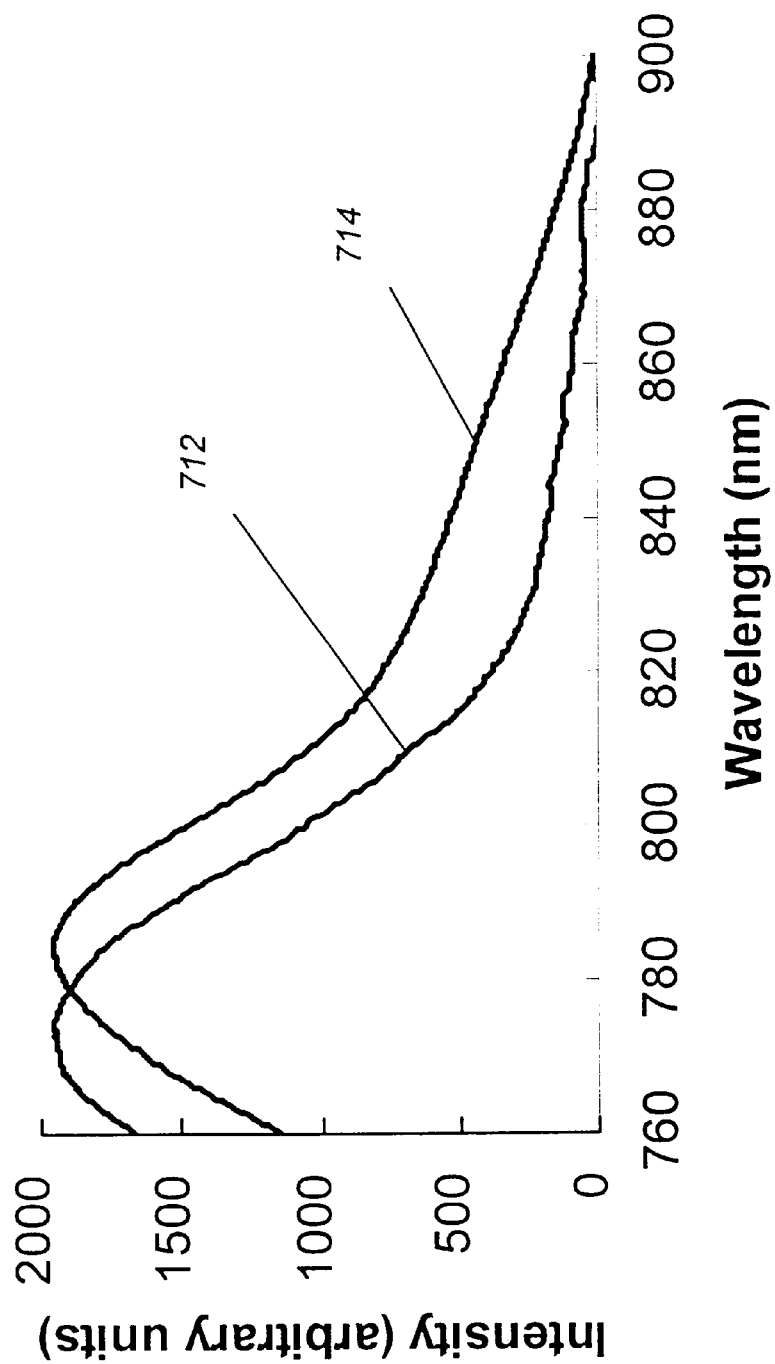
FIG. 14 shows the spectra of two Cy Dyes with differing emission spectra.

The same effect can also be achieved by using two fluorescent dyes with different optical characteristics, such as different fluorescent spectra, different fluorescent lifetimes, and so on, rather than two dyes with differing absorbence. As an example, the spectra of two fluorescent dyes, Cy 7 and Cy 7 with antibody, are shown in FIG. 14, where spectrum 712 and 714 represent the two forms of the Cy dye, without and with antibody, respectively.

Higher numbers of dyes can be used, and their concentrations imaged by solving a series of intensity measurements as N simultaneous equations, where N is the number of dyes, and N—1 is the number of additional filters required. Of note, if the dye emission bands are sufficiently discrete, an image taken through several bandpass filters may be used to detect each dye.

Example 10

Colorimetric Depth Determination

Engine 184 may use spectroscopic signals from the contrast agent in order to determine signal depth. This is possible as tissue absorbs different wavelengths of light in an unequal manner. For example, the transmitted signal from a contrast agent will change in shape as the signal passes through increasing thicknesses of tissue, and this can be used to generate a depth signal using one or more contrast agents. A basic feature of light is that the longer wavelengths tend to scatter less than light of shorter wavelengths. As a result, the bluer wavelengths of light tend to travel farther through tissue, and be relatively absorbed more. In addition, the human body has light absorbers in the blue to green wavelengths that causes tissue to absorb light more strongly in those wavelengths. Because of this unequal scattering and absorbence, the shorter (bluer) wavelengths of a transmitted signal tend to be relatively more absorbed with increasing distance. This results in the shorter wavelengths becoming increasingly under represented the farther a signal travels through tissue. As a result, the spectrum of light transmitted through tissue light changes with the depth of the signal source.

By knowing the spectrum of an emitter prior to passage through tissue, this effect can be used to determine the approximate or weighted mean depth of a target signal. In practice, this may be determined by measuring the target signal in different wavelength regions, such as by using two or more different filters in rapid sequence. The same result can be obtained using two or more dyes targeted to the same site, and measuring the relative brightness of each. Analysis methods used by the contrast locator may involve spectral features, such as peak wavelength, slope of a spectral region, or ratios of wavelengths.

Figure 15A:
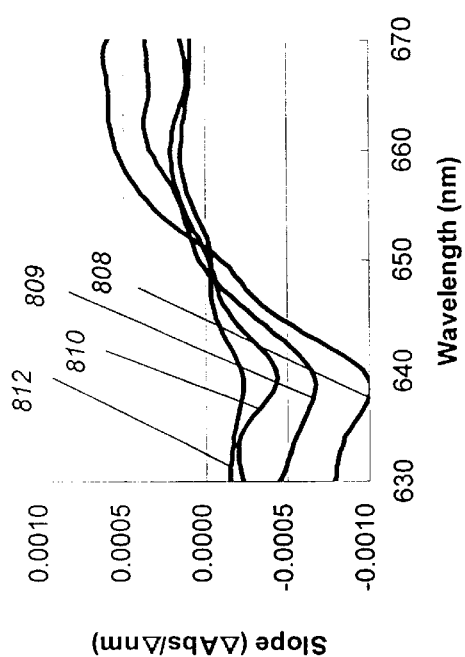
FIGS. 15A–B show the effect of target tissue depth on detected spectrum.
Figure 15B:
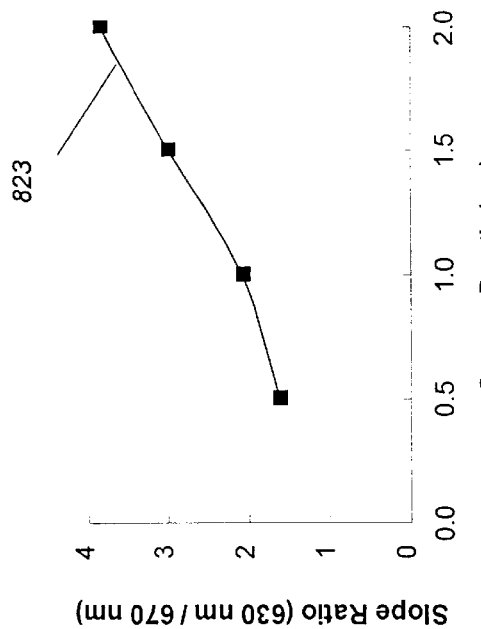

Thus, one simple type of a depth measurement is the ratio of a transmitted signal at two wavelengths. In this case, the shorter wavelengths are preferentially absorbed, making the ratio of the longer over the shorter wavelengths rise with increasing depth of signal. For example, FIG. 15A shows the measured first differential signal of a red light-emitting diode (a model for the red or near-infrared light emitted by a fluorescent marker) as the red light passes through increasing depths of a light-scattering lipid emulsion before detection. A first differential plot of the detected spectrum is used to correct in part for the effects of changes in baseline between the different measurements. In this example, the detected spectrum of the red diode changes with depth from the source, changing from shallow depth spectrum 808 at a distance of 0.5 cm from the source, to intermediate spectra 809 and 810 at depths of 1.0 and 1.5 cm, respectively, and finally to deeper depth spectrum 812 at a depth of 2 cm from the source. A ratiometric plot of the value first differential (or slope of absorbence) signal at 669 nm divided by the first differential signal at 635 nm is plotted against the depth of the signal from the detector is shown as FIG. 15B. In this figure, ratio response curve 823 shows that as the shorter wavelengths are relatively more attenuated, the ratio of the longer to the shorter wavelength value increases with increasing depth of the signal. Using ratio curve 823, the depth of a fluorescent source with a similar wavelength profile can be estimated using the ratio of the signal at 635 vs. 669 nm, independent of the intensity of the signal.

Measurement of the intensity of fluorescence of a single dye at two or more regions of the emission spectrum, with a ratio response curve determined for each dye type, may also be used as a measure of depth of the target tissue. Of note, the same type of ratiometric method can be performed by using two dyes, with peaks spaced farther apart, thus increasing the change in the ratio with depth provided that the peaks do not correspond to local maxima in variable concentration body components such as blood.

We have discovered an improved method and device that measures an induced optical signal from living tissue and allows the detection, localization, imaging, and targeting of contrast-enhanced tissues within the human body in room light, using light emitted from the body after illumination by a light source. A system constructed in accordance with the invention has been built and the method tested in several configurations in models, animals, and humans, and these have immediate application to several important problems, both medical and industrial, and thus constitutes an important advance in the art.

What is claimed is:

1. A method of detecting a target tissue within a living subject in ambient light, comprising:
   (a) illuminating the subject in ambient light with additional light from a light source gated to illuminate for a predetermined period, said source selected such that a target tissue may interact with and modify the illuminating light;
   (b) providing a gated light detector;
   (c) optically coupling the light detector to the subject;
   (d) gating the detector and synchronizing said gating with the light source gating, said gating performed such that the detector detects light substantially enriched in said modified light with respect to said ambient light for substantially the same said predetermined period;
   (e) determining a measurable parameter of said target tissue using an analysis of the detected light, said parameter being more accurately or reliably determinable with said gating; and, (f) generating an output signal in response to said determination.

2. The method of claim 1, wherein said detector is an imaging digital camera and said output signal is an image.

3. The method of claim 1 including the step of illuminating with additional light illuminates in short light pulses synchronized with detector gating.

4. A method of imaging target cells within a living subject in ambient light by enhancing the weak native signal of the target cells, comprising:

(a) administering to the subject an optical contrast agent, said agent selected so as to provide measurable contrast for said target cells in vivo;

(b) waiting until said contrast agent has achieved sufficient functional distribution and localization within the body;

(c) illuminating the subject with light from a light source, said light source selected such that the contrast agent in vivo may interact with and modify the illuminating light, and said light source further arranged so as to be temporally variable in intensity;

(d) providing a time-gated camera optically coupled to said subject, and using said camera to monitor or image said subject;

(e) synchronizing the gating of said camera as a function of said temporal variations of light source intensity such that said camera detects light enriched in said modified light with respect to ambient light for substantially the same temporal variations;

(f) determining a measurable parameter of the target cells using the detected light based upon a function of the distribution and localization of said contrast agent; and, (g) generating an output signal in response to said determination.

5. A system for externally or internally measuring a target tissue within the body of a living subject in background room light, comprising:

(a) an optical contrast agent for providing a source of contrast, said agent selected so as to provide a differential contrast between said target tissue and other tissues, and said agent administered to the subject so as to have achieved distribution and localization within the body;

(b) a gated light source for illuminating a portion of said subject with illuminating radiation for a predetermined period, said distributed contrast agent at least potentially disposed to interact with and modify said illuminating radiation;

(c) a gated light collector for collecting a portion of said modified radiation for substantially the same said predetermined period, said gated portion enriched in said modified radiation with respect to said background radiation, and for providing a detected signal in response to said collected portion;

(d) means for determining a measurable parameter of said target tissue based upon said detected signal, said measure based upon a measurement function of said distribution and localization of said contrast agent; and (e) means for generating an output signal in response to said determination.

6. The system of claim 5, wherein said background room light is the ambient light in a surgical operating room.

7. The system of claim 5, wherein said light source is further comprised of multiple light sources.

8. The system of claim 5, wherein said illuminating radiation has at least one wavelength between 200 nm and 2 $\mu$m.

9. The system of claim 5, wherein said light collector is further comprised of multiple light detector elements.

10. The system of claim 9, wherein said multiple detector elements comprise an ICCD digital camera.

11. The system of claim 5, wherein said measurable parameter is the presence or absence of said target tissue in the body.

12. The system of claim 5, wherein said measurable parameter is a localization of said target tissue within the body in at least one dimension.

13. The system of claim 12, wherein said localization is a direction of said target tissue.

14. The system of claim 12, wherein said localization is a distance to said target tissue.

15. The system of claim 12, wherein said localization is a function of the depth of said target tissue.

16. The system of claim 5, wherein said measurement function is an image of the distribution of said target tissue within a region of the body.

17. The system of claim 5, wherein said measurement function is based upon an optical feature selected from the group of features consisting of absorbence, fluorescence, Raman shift, excitation-emission maps, optical rotation, fluorescence decay, phase shift, time delay, or other optical features related to the interaction of said contrast agent with said illuminating radiation.

* * * * *